(12) United States Patent
Wang et al.

(10) Patent No.: US 8,173,406 B1
(45) Date of Patent: May 8, 2012

(54) DECONSTRUCTING LIGNOCELLULOSIC BIOMASS WITH A TWO-STEP METHOD

(75) Inventors: Bin Wang, Middlesex, MA (US); Hao Feng, Urbana, IL (US); Xiaojuan Wang, Champaign, IL (US); Bin Zhou, Urbana, IL (US); Jose Atilio De Frias, Urbana, IL (US)

(73) Assignee: The Board of Trustees of the University of Illinios, Urbana, IL (US)

( * ) Notice: Subject to any disclaimer, the term of this patent is extended or adjusted under 35 U.S.C. 154(b) by 245 days.

(21) Appl. No.: 12/642,601

(22) Filed: Dec. 18, 2009

Related U.S. Application Data

(60) Provisional application No. 61/138,927, filed on Dec. 18, 2008.

(51) Int. Cl.
*C12P 7/10* (2006.01)
*C12P 7/08* (2006.01)
*C12P 7/06* (2006.01)
(52) U.S. Cl. .................. 435/165; 435/161; 435/163
(58) Field of Classification Search .................. 435/161, 435/163, 165
See application file for complete search history.

(56) References Cited

OTHER PUBLICATIONS

Dadi, A. et al. (2007) "Mitigation of Cellulose Recalcitrance to Enzymatic Hydrolysis by ionic Liquid Pretreatment," Applied Biochemistry and Biotechnology 136-140:407-421.
De Vrije, T. et al. (2002) "Pretreatment of Miscanthus for hydrogen production by *Thermotoga elfii*," Intl J Hydro Energy 27:1381-1390.
Dien, B. et al. (2008) "Enzyme characterization for hydrolysis of AFEX and liquid hot-water pretreated distillers' grains and their conversion to ethanol," Bioresource Technology 99:5216-5225.
Eggeman, T. and Elander, R. (2005) "Process and economic analysis of pretreatment technologies," Bioresource Technology 96:2019-2025.
Galbe, M. and Zacchi, G. (2007) "Pretreatment of Lignocellulosic Materials for Efficient Bioethanol Production," Adv Biochem Engin/ Biotechnol 108:41-65.
Kim, K. and Hong, J. (2001) "Supercritical CO2 pretreatment of lignocellulose enhances enzymatic cellulose hydrolysis," Bioresource Technology 77:139-144.
Kim, S. and Holtzapple, M. (2005) "Lime pretreatment and enzymatic hydrolysis of corn stover," Bioresource Technology 96:1994-2006.
Kim, T. and Lee, Y. (2005) "Pretreatment and fractionation of corn stover by ammonia recycle percolation process," Bioresource Technology 96:2007-2013.
Lloyd, T. and Wyman, C. (2005) "Combined sugar yields for dilute sulfuric acid pretreatment of corn stover followed by enzymatic hydrolysis of the remaining solids," Bioresource Technology 96:1967-1977.
Mascarenhas, M. et al. (2000) "Characterization of Plant Carbohydrates and Changes in Leaf Carbohydrate Chemistry Due to Chemical and Enzymatic Degradation Measured by Microscopic ATR FT-IR Spectroscopy, " Applied Spectroscopy 54(5):681-686.
Mosier, N. et al. (2005) "Features of promising technologies for pretreatment of lignocellulosic biomass," Bioresource Technology 96:673-686.
Mosier, N. et al. (2005) "Optimization of pH controlled liquid hot water pretreatment of corn stover," Bioresource Technology 96:1986-1993.
Moure, A. et al. (2006) "Advances in the manufacture, purification and applications of xylo-oligosaccharides as food additives and nutraceuticals," Process Biochemistry 41:1913-1923.
Murnen, H. et al. (2007) "Optimization of Ammonia Fiber Expansion (AFEX) Pretreatment and Enzymatic Hydrolysis of Miscanthus x giganteus to Fermentable Sugars," Biotechnol. Prog. 23:846-850.
Murugesan, S. and Linhardt, R. (2005) "Ionic Liquids in Carbohydrate Chemistry-Current Trends and Future Directions," Current Organic Synthesis 2:437-451.
Oh, S. et al. (2005) "Crystalline structure anaylsis of cellulose treated with sodium hydroxide and carbon dioxide by means of X-ray diffraction and FTIR spectroscopy," Carbohydrate Research 340:2376-2391.
Ohgren, K. et al. (2007) "Effect of hemicellulose and lignin removal on enzymatic hydrolysis of steam pretreated corn stover," Bioresource Technology 98:2503-2510.
Wyman, C. (2007) "What is (and is not) vital to advancing cellulosic ethanol," Trends in Biotechnology 25(4):153-157.
Wyman, C. et al. (2005) "Coordinated development of leading biomass pretreatment technologies," Bioresource Technology 96:1959-1966.
Xiao, B. et al. (2001) "Chemical, structural, and thermal characterizations of alkali-soluble lignins and hemicelluloses, and cellulose from maize stems, rye straw, and rice straw," Polymer Degradation and Stability 74:307-319.
Xu, F. et al. (2006) "Comparative study of organosolv lignins from wheat straw," Industrial Crops and Products 23:180-193.
Yang, B. and Wyman, C. (2004) "Effect of Xylan and Lignin Removal by Batch and Flowthrough Pretreatment on the Enzymatic Digestibility of Corn Stover Cellulose," Biotechnology and Bioengineering 86(1):88-95.

*Primary Examiner* — Maryam Monshipouri
(74) *Attorney, Agent, or Firm* — Morrison & Foerster LLP

(57) ABSTRACT

Lignocellulosic biomass is noted for its recalcitrance to deconstruction as a feedstock for biofuel production. A two-step pretreatment method with the aim of enhancing cellulose digestibility, bypassing the traditional severe pretreatment reaction conditions and improving the overall economics of biofuel production is disclosed herein. A $1^{st}$ pretreatment step is used to partially remove hemicellulose and lignin. A $2^{nd}$ pretreatment step using electrolyzed water is used to break the crystalline structure and to remove residual hemicellulose and lignin before enzymatic hydrolysis for releasing fermentable sugars. A digestibility of 95% can be achieved by the two-step approach.

19 Claims, 12 Drawing Sheets

DECONSTRUCTING LIGNOCELLULOSIC BIOMASS WITH A TWO-STEP METHOD

RELATED APPLICATION

This application claims priority to U.S. Application Ser. No. 61/138,927 filed Dec. 18, 2008 which is hereby incorporated by reference in its entirety.

FIELD

This application relates to a two-step method for the pretreatment of lignocellulosic biomass to prepare the cellulose of the lignocellulosic biomass for further processing into fermentable sugars. Specifically, in the first pretreatment step hemicellulose and lignin are removed and can be used for the production of value-added products. A second pretreatment step with electrolyzed water, under relatively mild conditions, is used to further loosen lignocellulose so that the cellulose-enriched solids become more susceptible to cellulase digestion.

BACKGROUND

Due to the inevitable depletion and negative environmental impact of fossil fuels on the environment, increasing attention has been focused on converting feedstocks into renewable biofuels. Lignocellulosic biomass is a feedstock of particular interest. During the conversion process, pretreatment provides the key to unlocking the protective structures in biological feedstocks so that enzymatic hydrolysis of the carbohydrate fraction to monosugars can be achieved more rapidly and with greater yield (Wyman, 2007; Yang and Wyman, 2008). Cellulose in lignocellulosic biomass exists in the form of fiber, macrofibril, and microfibril which are surrounded by lignin and hemicellulose (Somerville et al., 2004). Some researchers attribute the recalcitrance of lignocellulosic biomass to two main root causes: 1) the presence of the lignin seal and hemicellulose links on the surface of cellulose which prevent cellulase from accessing the substrate, and 2) low accessibility of crystalline cellulose fibers, which restricts cellulase from working efficiently (Zhang et al., 2007). During pretreatment the matrix is broken to expose cellulose fibers for enzymatic attack.

In cellulosic ethanol production, processing accounts for up to 67% of the total cost with pretreatment being the single most expensive unit operation (Wyman, 2007). Researchers are scrutinizing each step in biomass conversion to minimize biofuel production costs. Similar to its successful counterpart in the petrochemical industry, the ultimate goal of a biorefinery is the efficient fractionation of lignocellulosic biomass into multiple product streams that contain value-added compounds so that the overall economics of a biofuel production facility can be significantly improved.

Numerous pretreatment concepts have been proposed and tested over the years. Steam treatment, or steam explosion, with and without the addition of a catalyst is one of the oldest methods that has been investigated for the pretreatment of a variety of lignocellulosic biomass feedstocks for the production of fuel ethanol (Soderstrom et al., 2004; Palmarola-Adrados et al., 2004; Sassner et al., 2005; Varga et al., 2004). Other treatment methods studied include supercritical $CO_2$ (Kim and Hong, 2001), supercritical water (Nakata et al., 2006), wet oxidation (Palonen et al., 2004), alkaline peroxide (Sun et al., 2000; Saha and Cotta, 2006), and hypochlorite treatment under acidic conditions (Hromadkova and Ebringerova, 1995).

A coordinated study supported by a USDA Initiative for Future Agricultural and Food Systems grant has examined the performance of promising biomass pretreatment methods. Using a single feedstock, common analytical protocols and consistent data interpretation, five research teams documented the technical and economical feasibility of six pretreatment techniques (Wyman et al., 2005; Eggeman and Elander, 2005). Almost all six of the pretreatment methods, including dilute acid (Lloyd and Wyman, 2005), flow through (Liu and Wyman, 2005), hot water (neutral pH) (Mosier et al., 2005a), ammonia fiber/freeze explosion (AFEX) (Teymouri et al., 2005), ammonia recycle percolation (ARP) (Kim and Lee, 2005), and lime (Kim and Holtzapple, 2005) are capable of producing high sugar yield. However, it was found that low cost pretreatment reactors are often counterbalanced by the high cost associated with either pretreatment catalyst recovery or ethanol recovery (Eggeman and Elander, 2005). Moreover, pretreatments at high temperatures, especially those treatments using acid or water, may cause degradation of valuable cellulose, hemicellulose and lignin. They can also result in the formation of inhibitory products that are toxic to microorganisms used for subsequent fermentation of the recovered sugar (Zaldivar and Ingram, 1999; Oliva et al., 2003).

Until now, all of the existing and newly developed biomass deconstruction methods have required harsh treatment conditions, extensive treatment times, high processing costs, or high energy consumption. As a result, it is very difficult to lower both the capital investment and production costs to produce biofuels with a price that is comparable to or lower than starch and petroleum-based fuels. As such, there is a tremendous need to develop improved methods for biomass deconstruction.

SUMMARY

A method for fractionating lignocellulosic biomass is provided. In one embodiment, the method includes preparing lignocellulosic biomass for enzymatic digestion. The method may include (a) providing lignocellulosic biomass; (b) mixing the lignocellulosic biomass with a 1 to 4% alkaline peroxide solution at a pH of 10 to 13 to form a slurry; (c) separating the slurry into a solid precipitate and a supernatant; (d) washing the solid precipitate to produce a neutralized (pH 5 to 8) solid precipitate; and (e) treating the neutralized solid precipitate with acidic electrolyzed water at a pH of 2 to 4 or alkaline electrolyzed water at a pH from 8 to 13 to prepare the lignocellulosic biomass for enzymatic digestion.

In a further embodiment, a method of hydrolyzing lignocellulosic biomass with an enzyme is provided. The method may include (a) providing lignocellulosic biomass; (b) mixing the lignocellulosic biomass with a 1 to 4% alkaline peroxide solution at a pH of 10 to 13 to form a slurry; (c) separating the slurry into a solid precipitate and a supernatant; (d) washing the solid precipitate to produce a neutralized solid (pH 5 to 8); (e) treating the neutralized solid precipitate with acidic electrolyzed water at a pH of 2 to 4 or alkaline electrolyzed water at a pH of 8 to 13 to form an electrolyzed water-treated precipitate; and (f) hydrolyzing the electrolyzed water-treated precipitate with an enzyme. In a further embodiment, the enzyme is cellulase.

In a further embodiment, the method includes (a) providing lignocellulosic biomass wherein the lignocellulosic biomass includes cellulose, lignin and hemicellulose; (b) treating the lignocellulosic biomass with a solvent to produce a first solubilized fraction of lignin and hemicellulose, and a first residue including cellulose, lignin and hemicellulose wherein the weight ratio of cellulose to cellulose+lignin+hemicellulose of the first residue is greater than the weight ratio of cellulose to cellulose+lignin+hemicellulose in the provided lignocellulosic biomass; and (c) treating the first residue with electrolyzed water to produce a second solubilized fraction of lignin and hemicellulose, and a second residue including cellulose, lignin and hemicellulose.

The method may further include (d) wherein the second residue and the second solubilized fraction from (c) are hydrolyzed with cellulase. The cellulase may include Celluclast 1.5 L, Novozyme 188, or Spezyme CP, or Accellerase 1000.

In a further embodiment, the second residue may be separated from the second solubilized fraction after (c). Separation may be achieved through centrifugation, filtration or other suitable fractionation means. The separated second residue may be hydrolyzed with cellulase. Lignin and hemicellulose may be recovered from the separated second solubilized fraction.

The lignocellulosic biomass may include one or more of *Miscanthus* plant material, switchgrass, cord grass, rye grass, reed canary grass, common reed, wheat straw, barley straw, canola straw, oat straw, corn stover, soybean stover, oat hulls, sorghum, rice hulls, sugar cane bagasse, corn fibre, Distiller's Dried Grains with Solubles (DDGS), corn cobs, pine, willow, aspen, poplar wood, and energy cane.

The solvent may be hydrogen peroxide. The concentration of the hydrogen peroxide may be 1-4%. The pH of the solvent may be in the range of 10-13.

The method of step (b) may be performed at a temperature of up to 100° C. and for up to 48 hours.

In the method, the electrolyzed water may be acidic electrolyzed water (AEW). The pH of the AEW may be in the range of pH 2-4 with an oxidation-reduction potential of up to 1170 mV. In preferred embodiments, the pH is approximately 2.6.

In another embodiment of the method, the electrolyzed water may be alkaline electrolyzed water (ALEW). The pH of the ALEW may be from pH 8-13 with an oxidation-reduction potential of up to −795 mV. In preferred embodiments, the pH is approximately 11.4.

In another embodiment, the method of step (c) is performed at a temperature of 100-140°. In a preferred embodiment, the temperature is approximately 121° C.

In another embodiment, the method of step (c) is performed for up to 2 hours. In a preferred embodiment, the method is performed for approximately 50 minutes.

In a preferred embodiment, the solid to liquid loading ratio of the lignocellulosic biomass to solvent is 3-15%. In a preferred embodiment, the solid to liquid loading ratio is approximately 5%.

In another embodiment, the solid to liquid loading ratio of the first residue to the electrolyzed water is 5-20%. In a preferred embodiment, the solid to liquid loading ratio is approximately 6.25%.

In one embodiment, the solvent is an alkaline aqueous solution. In a further embodiment, the alkaline aqueous solution is sodium hydroxide, potassium hydroxide, or urea.

In one embodiment, the solvent is an acid. The acid may be an inorganic acid or an organic acid. In a further embodiment, the acid is phosphoric acid, hydrochloric acid, sulphuric acid, nitric acid, citric acid or acetic acid.

In one embodiment, the solvent is an organic solvent. In a further embodiment, the organic solvent is alcohol, ketone, dimethyl sulfoxide (DMSO), or dioxane.

In a preferred embodiment, a method is provided for fractionating lignocellulosic biomass. The method includes (a) providing lignocellulosic biomass wherein the lignocellulosic biomass cellulose, lignin and hemicellulose; (b) treating the lignocellulosic biomass with a solvent to produce a first solubilized fraction of lignin and hemicellulose, and a first residue including cellulose, lignin and hemicellulose wherein the weight ratio of cellulose to cellulose+lignin+hemicellulose of the first residue is greater than the weight ratio of cellulose to cellulose+lignin+hemicellulose in the provided lignocellulosic biomass; (c) separating the first residue from the first solubilized fraction; and (d) treating the first residue with electrolyzed water to produce a second solubilized fraction of lignin and hemicellulose, and a second residue including cellulose, lignin and hemicellulose.

The method may further include (e) wherein the second residue and the second solubilized fraction from (d) are hydrolyzed with cellulase. The cellulase may include Celluclast 1.5 L, Novozyme 188, or Spezyme CP, or Accellerase 1000.

In a further embodiment, the second residue may be separated from the second solubilized fraction after (d). Separation may be achieved through centrifugation, filtration or other suitable fractionation means. The separated second residue may be hydrolyzed with cellulase. Lignin and hemicellulose may be recovered from the separated second solubilized fraction.

In a further embodiment, the lignocellulosic biomass may include one or more of *Miscanthus* plant material, switchgrass, cord grass, rye grass, reed canary grass, common reed, wheat straw, barley straw, canola straw, oat straw, corn stover, soybean stover, oat hulls, sorghum, rice hulls, sugar cane bagasse, corn fibre, Distiller's Dried Grains with Solubles (DDGS), corn cobs, pine, willow, aspen, poplar wood, and energy cane.

The solvent may be hydrogen peroxide. The concentration of the hydrogen peroxide may be 1-4%. The pH of the solvent may be in the range of 10-13. The method of step (b) may be performed at a temperature of up to 100° C. and for up to 48 hours.

In the method, the electrolyzed water may be AEW. The pH of the AEW may be in the range of pH 2-4 with an oxidation-reduction potential of up to 1170 mV. In preferred embodiments, the pH is approximately 2.6.

In another embodiment of the method, the electrolyzed water may be ALEW. The pH of the ALEW may be from pH 8-13 with an oxidation-reduction potential of up to −795 mV. In preferred embodiments, the pH is approximately 11.4.

In another embodiment, the method of step (d) is performed at a temperature of 100-140°. In a preferred embodiment, the temperature is approximately 121° C.

In another embodiment, the method of step (d) is performed for up to 2 hours. In a preferred embodiment, the method is performed for approximately 50 minutes.

In a preferred embodiment, the solid to liquid loading ratio of the lignocellulosic biomass to solvent is 3-15%. In a preferred embodiment, the solid to liquid loading ratio is approximately 5%.

In another embodiment, the solid to liquid loading ratio of the first residue to the electrolyzed water is 5-20%. In a preferred embodiment, the solid to liquid loading ratio is approximately 6.25%.

In one embodiment, the solvent is an alkaline aqueous solution. In a further embodiment, the alkaline aqueous solution is sodium hydroxide, potassium hydroxide, or urea.

In one embodiment, the solvent is an acid. The acid may be an inorganic acid or an organic acid. In a further embodiment, the acid is phosphoric acid, hydrochloric acid, sulphuric acid, nitric acid, citric acid or acetic acid.

In a further embodiment, the solvent is an organic solvent. In a further embodiment, the organic solvent is alcohol, ketone, dimethyl sulfoxide (DMSO), or dioxane.

In a preferred embodiment, a method for the pretreatment of lignocellulosic biomass to expose cellulose for further processing is provided. The method may include (a) mixing lignocellulosic plant material with a 4.0% alkaline peroxide solution at a pH of 11.5 to form a slurry; (b) incubating the slurry for a period of time sufficient to remove a portion of hemicellulose and lignin; (c) separating the slurry into a solid and a supernatant; (d) washing the solid with water to produce neutralized solid; and (e) treating the neutralized solid with electrolyzed water for a period of time sufficient to expose cellulose fiber from the lignocellulosic biomass for further processing.

In a further embodiment, the lignocellulosic biomass is Miscanthus plant material, switchgrass, cord grass, rye grass, reed canary grass, common reed, wheat straw, barley straw, canola straw, oat straw, corn stover, soybean stover, oat hulls, sorghum, rice hulls, sugar cane bagasse, corn fibre, Distiller's Dried Grains with Solubles (DDGS), corn cobs, pine, willow, aspen, poplar wood and energy cane.

In a further embodiment, step (b) is performed for up to 24 hours with shaking at 50° C. In yet a further embodiment, step (e) is performed for up to 50 minutes at 121° C.

In one embodiment, the alkaline peroxide is hydrogen peroxide.

In the method, the electrolyzed water may be AEW. The pH of the AEW may be in the range of pH 2-4 with an oxidation-reduction potential of up to 1170 mV. In preferred embodiments, the pH is approximately 2.6.

In another embodiment of the method, the electrolyzed water may be ALEW. The pH of the ALEW may be from pH 8-13 with an oxidation-reduction potential of up to −795 mV. In preferred embodiments, the pH is approximately 11.4.

In a preferred embodiment, the solid to liquid loading ratio of the lignocellulosic biomass to solvent is 3-15%. In a preferred embodiment, the solid to liquid loading ratio is approximately 5%.

In another embodiment, the solid to liquid loading ratio of the neutralized solid to the electrolyzed water is 5-20%. In a preferred embodiment, the solid to liquid loading ratio is approximately 6.25%.

DETAILED DESCRIPTION

Recently, lignocellulosic biomass has become an attractive feedstock for the production of alternative energy. However, due to the recalcitrant nature of the plant material, accessing the useful sugar contained in the biomass has been challenging. The sugars must first be "unlocked" from protective barriers before they can be utilized for energy production.

Plant cells are protected by a rigid cell wall composed of carbohydrate polymers. A major structural component of the cell wall is cellulose, a glucose polymer that exists in the form of a microfibril. Cellulose microfibrils are connected through extensive hemicellulose linkages. The hemicellulose is also bound to lignin which forms a protective barrier around the microfibril. Collectively, any biomass that contains cellulose, hemicellulose and lignin is referred to as lignocellulosic biomass. The extensive crosslinking between the polysaccharides and lignin makes the lignocellulosic biomass highly resistant to degradation. To extract the fermentable sugars, the lignin contacts have to be broken.

Once the cellulose is separated from lignin and hemicellulose, the cellulose polymer needs to be broken down into simple monosaccharides for fermentation. The cellulose polymer is typically hydrolyzed to obtain the glucose subunits which can then be fermented for the production of ethanol.

Unlike glucose from cellulose, xylose which is a major component of hemicellulose, is difficult to ferment. When considering large-scale economical production of fuel ethanol from hemicellulose-rich biomass feedstocks, fermentation of xylose is a major concern. Currently the most commonly used industrial fermentation microorganisms basically only ferment glucose. (Hahn-Hägerdal et al., 2006).

On the other hand, the temperature used to break down hemicellulose to release pentoses is lower than that needed to alter the crystalline structure of cellulose. As a result, when pretreating biomass at a temperature high enough to break the crystalline structure of cellulose, it will inevitably cause degradation of pentoses and generate inhibitory compounds such as furfural (Öhgren et al., 2005; Qian et al. 2005; Usuki et al. 2008). It is therefore advantageous to remove, or partially remove, hemicellulose before a pretreatment step targeted at loosening the cellulose structure to significantly reduce sugar loss and inhibitor formation.

Figure 1:
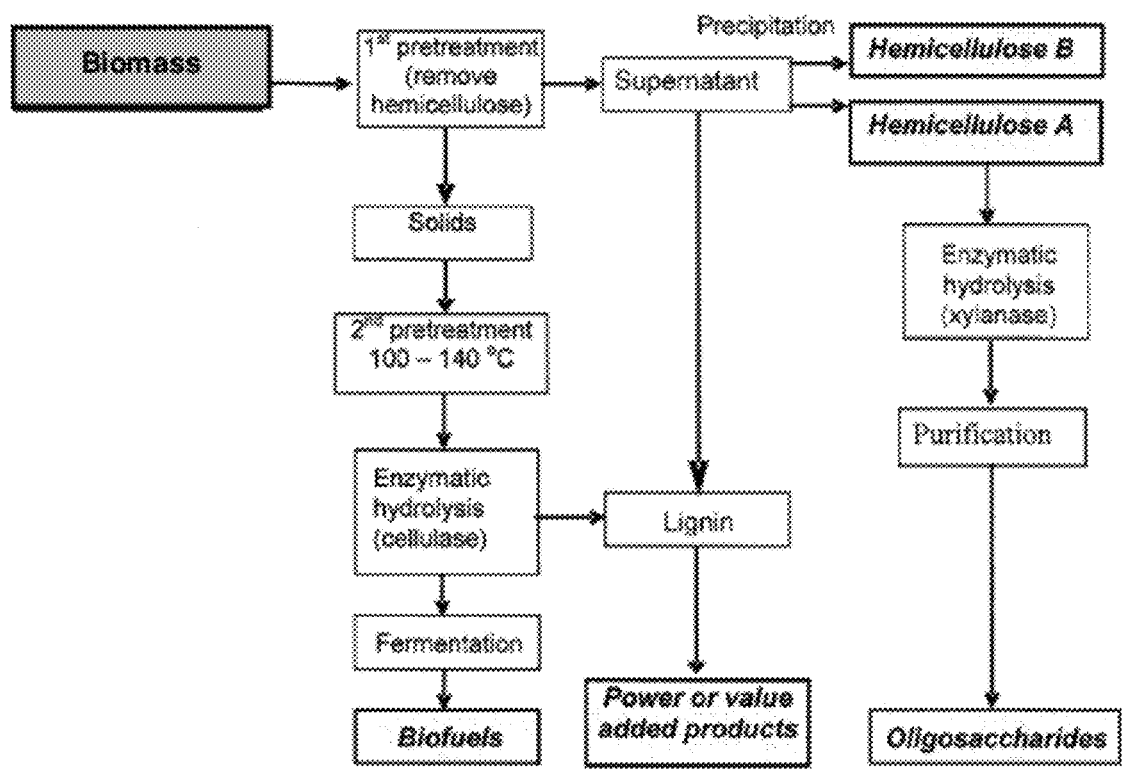
FIG. 1 is a conceptual flowchart illustrating a two-step process for the fractionation of lignocellulosic biomass for the production of biofuel and other value-added products.

In order to overcome the natural recalcitrance of lignocellulosic biomass, bypass harsh pretreatment conditions and improve the overall economics of biofuel production, we propose a two-step lignocellulose biomass pretreatment method (FIG. 1). The first pretreatment step is to partially remove hemicellulose and lignin from the lignocellulosic biomass with hydrogen peroxide or other select catalysts to expose crystalline cellulose fibers. The now-exposed crystalline cellulose fibers are then subjected to a second pretreatment step using electrolyzed water as the catalyst to break the crystalline structure and to remove residual lignin and hemicellulose. This two-step treatment method increases the accessibility of the cellulose to cellulases in the subsequent enzymatic hydrolysis step to release fermentable sugars.

The objective of using a solvent such as hydrogen peroxide coupled with electrolyzed water in the two-step pretreatment is different from that of a conventional one-step pretreatment method. In conventional one-step pretreatments, the goal is to maximize monosugar yield, including glucose and xylose, while the goal of the two-step method is to fractionate biomass for the production of value-added products in addition to glucose. Therefore, in the first step the aim is to partially remove hemicellulose and lignin. This will serve two purposes. First, the hemicellulose and lignin can be used for the production of value-added products. Second, after partial removal of hemicellulose and lignin, further treatment of the remaining biomass can be conducted at mild conditions to avoid sugar degradation and the generation of fermentation inhibitors. The initial solvent treatment, for example hydrogen peroxide treatment at low temperature, is suitable for hemicellulose removal and delignification whereas the subsequent electrolyzed water treatment at elevated temperature is effective at breaking crystalline cellulose fiber. The two-step pretreatment method utilizes the advantages of each catalyst to facilitate a new deconstruction process that is successful at producing high sugar yields.

As demonstrated by test results for the treatment of recalcitrant *Miscanthus* plant material, the sugar yield (95%) from the hydrogen peroxide and electrolyzed water two-step pretreatment is much higher than that from sulphuric acid treatment alone (82%) (see examples below). Since sulphuric acid is typically an effective catalyst, the low sugar yield from the sulphuric acid-pretreated *Miscanthus* plant material indicates the difficulty of deconstructing this energy crop. Notably, the sugar yield (95%) from the two-step pretreatment is unexpectedly higher than a pretreatment using any individual catalyst, including sulphuric acid, hydrogen peroxide or electrolyzed water alone.

An additional advantage of the two-step pretreatment process is the reduced cost in the final enzymatic hydrolysis step. If both cellulose and hemicellulose are to be converted into monomeric sugars, an enzyme mixture has to be used. Commercial cellulase and β-glucosidase are effective in converting cellulose into glucose but are usually ineffective at hydrolyzing hemicellulose such that other enzymes like pectinase and feruloyl esterase need to be supplemented, adding an increased expense to the already high enzyme cost. After the first pretreatment step (the hydrogen peroxide treatment), the remaining hemicellulose in the sample is easily hydrolyzed by cellulase and β-glucosidase to fermentable monosugars. The effect is even more apparent for samples pretreated with both hydrogen peroxide and alkaline electrolyzed water.

Two-Step Pretreatment Method

In the two-step pretreatment method, lignocellulosic biomass is first treated to remove a portion of the hemicellulose and lignin (See FIG. 1). Examples of suitable feedstocks for the lignocellulosic biomass include but are not limited to *Miscanthus* plant material, switchgrass, cord grass, rye grass, reed canary grass, common reed, wheat straw, barley straw, canola straw, oat straw, sorghum, corn stover, soybean stover, oat hulls, rice hulls, sugar cane bagasse, corn fibre, Distiller's Dried Grains with Solubles (DDGS), corn cobs, pine, willow, aspen, poplar wood, and energy cane.

Treatment methods that can be used to remove a first portion of the hemicellulose and lignin include but are not limited to steam explosion, treatment with alkaline aqueous solutions, acidic solutions, organic solvents, ionic liquids (IL), and combinations thereof. Examples of alkaline aqueous solutions include sodium hydroxide, potassium hydroxide, urea, or combinations thereof. Examples of acidic solutions include phosphoric acid, hydrochloric acid, sulphuric acid, nitric acid, acetic acid, and citric acid. Examples of organic solvents include alcohols, ketones, dimethyl sulfoxide (DMSO), and dioxane. In preferred embodiments, the lignocellulosic biomass is mixed with an alkaline peroxide solution. Suitable concentrations of alkaline peroxide are 1.0-4.0%. Suitable pHs are 10-14. In a preferred embodiment, the concentration of $H_2O_2$ is approximately 4% and the pH is 11.5.

In embodiments where a solvent will be used in the first treatment step, the solid to liquid (S/L) loading ratio is between 3-15%. The solid to liquid loading ratio is the percent of solid by weight in a mixture of liquid and solid. In a preferred embodiment, the S/L ratio is 5%. Once the slurry of lignocellulosic biomass and solution is formed, the reaction is incubated with heat for a period of time with shaking. The reaction can be incubated from 0-48 hours at a temperature between 0-100° C. with shaking (50-500 rpm). In a preferred embodiment, the slurry is incubated for 24 hours at 50° C. at 200 rpm.

After the incubation, the slurry is fractionated into supernatant and solid residue through centrifugation, filtration, or other suitable separation methods. The supernatant containing hemicellulose and lignin is removed. The remaining solid residue is then neutralized. The solid residue can be neutralized by washing with deionized water, Acidic Electrolyzed Water (AEW) or adjusting the pH chemically. The hemicellulose and its derivatives like xylo-oligosaccharides removed from the lignocellulose biomass during the $1^{st}$ pretreatment can be precipitated from the supernatant by an organic solvent (acetone, ethanol, etc) and used as value added products or hydrolyzed for biofuel production.

The neutralized solid residue is then pretreated with AEW or ALEW for 0-2 hours. In preferred embodiments, the pH of the AEW is 2-4 and the pH of ALEW is 10-12. Suitable temperatures for the electrolyzed water treatment step are between 100-140° C. Suitable S/L ratios are between 5-20%. In a preferred embodiment, the solid residue is incubated at 121° C. at an S/L of 6.25% for 50 min in an autoclave or in a suitable reactor. The pH of the sample can then be adjusted to conditions suitable for subsequent enzymatic hydrolysis by cellulases.

The ratio of the amount of cellulose to the amount of cellulose+to the amount of lignin+to the amount of hemicellulose can be calculated by a compositional and/or chemical analysis. Compositional and/or chemical analysis can be performed using techniques such as Fourier transform infrared (FTIR) spectroscopy and HPLC analysis. For FTIR, the composition of a lignocellulosic biomass (the amount of cellulose, the amount of lignin and the amount of hemicellulose) can be determined by measuring its infrared spectra using an FTIR spectrometer and then comparing the results with a commercially available or specifically prepared spectral data base, or with composition results from wet chemistry analysis.

For HPLC analysis, the standard methods developed by the National Renewable Energy Laboratory (NREL) can be used to determine the chemical composition of a lignocellulosic biomass (the amount of cellulose, the amount of lignin and the amount of hemicellulose). Another approach is to acquire nutritional composition data for the lignocellulosic biomass using the procedure, for instance developed by the Experiment Station Chemical Laboratories, University of Missouri. Both composition analysis methods produce data about the cellulose content in the lignocellulosic biomass, which can be used to determine the ratio of the amount of cellulose to entire biomass (the amount of cellulose plus the amount of hemicellulose plus the amount of lignin) after pretreatment or hydrolysis. For example, the cellulose to cellulose+hemicellulose+lignin ratio was 46:100 for the untreated lignocellulosic biomass from *Miscanthus* that was used in the examples disclosed herein. After the first pretreatment, the ratio increased to 45.7:60, which represents an increase of the cellulose percentage from 46% to 76%, thus demonstrating the effectiveness of the $1^{st}$ pretreatment in removing hemicellulose and lignin. The ratios are dimensionless because the weight units in the ratios cancel each other out when the ratio is calculated.

The cellulose ratio in the residue after the first pretreatment will be significantly higher than in the raw, untreated lignocellulosic biomass. Öhgren et al. (2007) examined the effect of hemicellulose and lignin removal on enzymatic hydrolysis of steam pretreated corn stover. The weight percentages of glucan (cellulose), xylan and lignin in the raw versus the pretreated corn stover were listed and correlated with cellulose digestibility. When the removal of xylan and lignin approached 50%, the glucose yield increased from 60% to approximately 90%. Yang and Wyman (2004) also investigated the effect of xylan and lignin removal on the enzymatic digestibility of corn stover by batch and flow through pretreatment. When 25.4% xylan and 12.1% lignin were removed, the cellulose digestibility was only 53.2%, but if 66.5% xylan and 47.3% lignin were removed before hydrolysis, the cellulose digestibility increased to 79.7%. Thus, it is estimated that cellulose digestibility could be significantly higher if the content of the amount of lignin+the amount of hemicellulose in the first residue is less than 50% percent of the original the amount of lignin+the amount of hemicellulose content in the original lignocellulosic biomass cellulose+the amount of hemicellulose+lignan.

After the $2^{nd}$ pretreatment step, the exposed cellulose polymer can be hydrolyzed by cellulases into monosugars. Cellulase such as commercially available Celluclast 1.5 L, Novozyme 188, or Spezyme CP, or Accellerase 1000, can be used to convert the cellulose polymer into its corresponding glucose subunits.

Glucose can then be fermented for the production of ethanol or butanol, by virtue of recent industrial fermentation practices that includes separate hydrolysis and fermentation (SHF) (the melle boinot process, cascade fermentation, biostil process, etc.), simultaneous saccharification and fermentation (SSF), coimmobilization of enzymes and microorganisms, and fermentation by mixed cultures.

Treatment of *Miscanthus*

The use of *Miscanthus* as a feedstock for the production of biofuel is a recent endeavour. *Miscanthus* is a woody rhizomatous C4 perennial grass species which grows rapidly and gives high yields per hectare. *Miscanthus* also has a long productive life time (10-15 years), low moisture content at harvest, high water and nitrogen use efficiencies and a low susceptibility to pests and diseases making it an ideal candidate for biofuel production (Jones and Walsh, 2001).

Preferred conditions and steps for the pretreatment of *Miscanthus* plant material with hydrogen peroxide and acidic electrolyzed water include: (a) mixing *Miscanthus* with a 4.0% alkaline peroxide solution at a pH of 11.5 to form a slurry; (b) incubating the slurry for 24 hours with shaking at 200 rpm at 50° C. to remove a portion of hemicellulose and lignin; (c) separating the slurry into a solid and a supernatant; (d) washing the solid with deionized water to produce neutralized solid; (e) treating the neutralized solid with acidic electrolyzed water (AEW) at a pH of 2.6 for 50 minutes at 121° C. to expose cellulose fiber from the *Miscanthus*.

EXAMPLES

Methods for a two-stage approach to fractionate *Miscanthus* biomass were tested. The first step was to partially remove hemicellulose and lignin for the production of value-added products. The remaining exposed cellulose fibers were then subjected to a second pretreatment step using electrolyzed water as the catalyst, followed by an enzymatic hydrolysis step to release fermentable sugars. The morphological and chemical changes of pretreated *Miscanthus* were elucidated by Scanning Electron Microscopy (SEM) and Fourier Transform Infrared Spectroscopy (FTIR). Cross-checking the micro-structural alterations by SEM and the corresponding chemical linkage changes by FTIR spectra provided a useful tool to understanding the biomass deconstruction process during pretreatment. All the data presented in the following examples demonstrated that *Miscanthus* is a recalcitrance feedstock.

In laboratory tests, we observed that the two-stage pretreatment approach significantly enhanced cellulose digestibility and shortened enzymatic hydrolysis time. The highest digestibility (95%) was achieved using an alkaline peroxide and alkaline electrolyzed water (ALEW) sequential pretreatments. From the SEM observations after the $1^{St}$ pretreatment, cellulose fibers were exposed to surroundings so that the $2^{nd}$ pretreatment temperature could be reduced to 121° C. to help minimize sugar loss and the formation of chemicals that inhibit biofuel fermentation. In addition, the disruption of the linkages between hemicellulose and lignin, as shown by FTIR curves, also helped render the residual hemicellulose highly digestible to cellulase.

Chemicals and Materials

*Miscanthus* was ground using a Thomas-Wiley mill (model 4) to pass a 1 mm sieve and stored under dry conditions until further use. The composition of Miscanthus, determined by the Experiment Station Chemical Laboratories, University of Missouri, was 46.0% cellulose, 27.8% hemicellulose and 10.7% lignin. Celluclase 1.5 L (cellulase) and Novozyme 188 (β-glucosidase) were purchased from Sigma.

All other reagents and chemicals of analytical grade were purchase from either Sigma Aldrich (St. Louis, Mo.) or Fisher Scientific (Pittsburgh, Pa.) unless otherwise stated. Percentage of chemicals and materials used was based on a w/w ratio unless otherwise stated.

Acidic electrolyzed water (AEW) and alkaline electrolyzed water (ALEW) were generated by a ROX-20TA-U water electrolyzer (Hoshizaki America, Inc., South Peachtree City, Ga.). A 24% solution of sodium chloride and de-ionized water from a laboratory supply line were simultaneously pumped into the generator chamber and the final concentration of sodium chloride solution passing through electrodes in the generator chamber was about 0.2%. When the strong acidic and alkaline indicators were on, AEW and ALEW were collected from the outlets with flasks. The AEW had a pH of 2.6 and an oxidation reduction potential (ORP) of >1,100 mV, while the ALEW had a pH of 11.4 and ORP of <−795 mV.

Example 1

One-Step Pretreatment

A one-step pretreatment was conducted in tubular reactors (1 inch OD×7 inch L) with a working volume of 50 mL. A SBL-2D fluidized sand bath (4,000W, Techne® Inc. Burlington, N.J.) was used to heat up the tubular reactors. The temperature control was facilitated with a TC-8D temperature controller. Five grams (dry weight) *Miscanthus* was mixed with a catalyst (1% $H_2SO_4$, AEW, or ALEW) to form a slurry. The *Miscanthus* slurry was loaded into the reactors that were submerged in the fluidized sand bath. The samples were then heated to either 170°, 180°, 190° or 200° C. and held for 8, 16, or 24 minutes. A test at 160° C. heated for 24 min and a test at 210° C. for 8 min were also conducted. The S/L loading ratio for all of the one-step pretreatment tests was 12.5%. After the pretreatment, the reactors were removed from the sand bath and immediately submerged in ice cold water to stop the reaction.

Example 2

Two-Step Pretreatment

In the two-step pretreatment, 5 g (dry weight) *Miscanthus* samples were first mixed with an alkaline peroxide solution (pH 11.5, hydrogen peroxide concentration of 1.0, 1.5, 2.0, 3.0, and 4.0%) in 100 mL Erlenmeyer flasks. The S/L loading ratio was brought to 5%. The reaction was performed in a Classic C76 water bath shaker (New Brunswick Scientific. New Brunswick, N.J.). The slurries were incubated for 24 hours at 200 rpm and 50° C. After the supernatants were removed, the solid residues were washed by DI water until the sample pH became neutral. The solids were then pretreated with AEW or ALEW at 121° C. and an S/L of 6.25% for 50 min in a NAPCO autoclave (Model 8000-DSE, Jouan Inc., Winchester, Va.). The total weight of the slurry was 80 g. The pH was adjusted to 5.0 with 5M NaOH (or HCl) solution before enzymatic hydrolysis.

Enzymatic Hydrolysis

Enzyme solutions were prepared in a citrate buffer (pH 5.0, 0.1M). The cellulase activity for a 1:1 blend of Celluclast 1.5 L and Novozyme 188 were determined following the NREL laboratory analytical procedure (LAP-006). Cellulase preparations (15 FPU/g cellulose) were used for all hydrolysis experiments. The slurries in 100 mL Erlenmeyer flasks were incubated in an Aquatherm water bath shaker (New Brunswick Scientific., New Brunswick, N.J.) for 168 hours at 200 rpm and 50° C. A 1.5 mL aliquot was sampled at regular intervals, and immediately heated in boiling water for 5 min to deactivate enzymes. Samples were subjected to centrifugation (9000×g) and then filtration (0.22 μm) before being frozen at −20° C. for later HPLC analysis. The percent digestibility was calculated according to NREL laboratory analytical procedures (LAP-008 and 009) as follows:

$$\% \text{ Digestibility} = \frac{[\text{Glucose}] + 1.053[\text{Cellobiose}]}{1.111 f [\text{Biomass}]} \times 100\%$$

where, [Glucose] is the residual glucose concentration (g/L); [Cellobiose] is the residual cellobiose concentration (g/L); [Biomass] is the dry biomass concentration at the beginning of the hydrolysis (g/L); and f is the cellulose fraction in dry biomass (g/g). The multiplication factor, 1.053, converts cellobiose to equivalent glucose.

HPLC Analysis

Sugar concentrations were determined by an HPLC system that consisted of a Waters (Milford, Mass., USA) 2695 Separation Module, a Waters 717 plus autosampler and a Waters 410 refractive index detector, monitored by an HP Chem Station computer program (Agilent Technologies, Germany). A Bio-Rad HPX-87P column (Bio-Rad Laboratories Inc., Hercules, Calif.) equipped with a guide column (30×4.6 mm) was used. The column temperature was kept at 85° C. The temperature of the refractive index detector was set at 35° C. The mobile phase was ultrapure water (18.1 MΩ cm) at a flow rate 0.6 mL/min. The correlation coefficient of sugar standard curves was greater than 0.998.

Statistics

All experiments were performed in triplicate. Using SAS software (version 9.1.3, SAS Institute, Cary, N.C.), the experimental data was analyzed by one-way ANOVA followed by LSD (t) pairwise comparison of means. The statistical significance level (P-value) was set at 0.05.

Scanning Electron Microscopy (SEM)

The *Miscanthus* samples before and after pretreatment were washed by DI water, dehydrated in a graded series of ethanol solutions (25, 50, 70, 95 and 100%) and dried in a $CO_2$ critical-point drier (Samdri-PVT-3D, Tousimis Research Corporation, Rockville, Md.). The dried samples were mounted on stubs and sputter-coated with gold/palladium for 70 seconds by a Desk II TSC turbo-pumped sputter coater (Denton Vacuum, Moorestown, N.J.). Scanning electron micrographs were obtained by an environmental scanning electron microscope (Philips XL30 ESEM-FEG, FEI Company, Eindhoven, Netherlands).

Fourier Transform Infrared Spectroscopy (FTIR)

The untreated, pretreated and hydrolyzed *Miscanthus* samples were washed thoroughly by DI water and oven-dried at 70° C. until a constant weight was achieved. Using a Thermo-Nicolet Nexus 670 spectrometer (Thermo Nicolet Corporation, Madison, Wis.) and its diffuse reflectance attachment, the diffuse reflectance Fourier transform infrared spectra (DRIFTS) of 25 mg samples were recorded in the range of 4000-800 $cm^{-1}$ with a resolution of 1 $cm^{-1}$ and 64 scans per sample.

*Miscanthus* Characterization and One-Step Pretreatment

Figure 2:
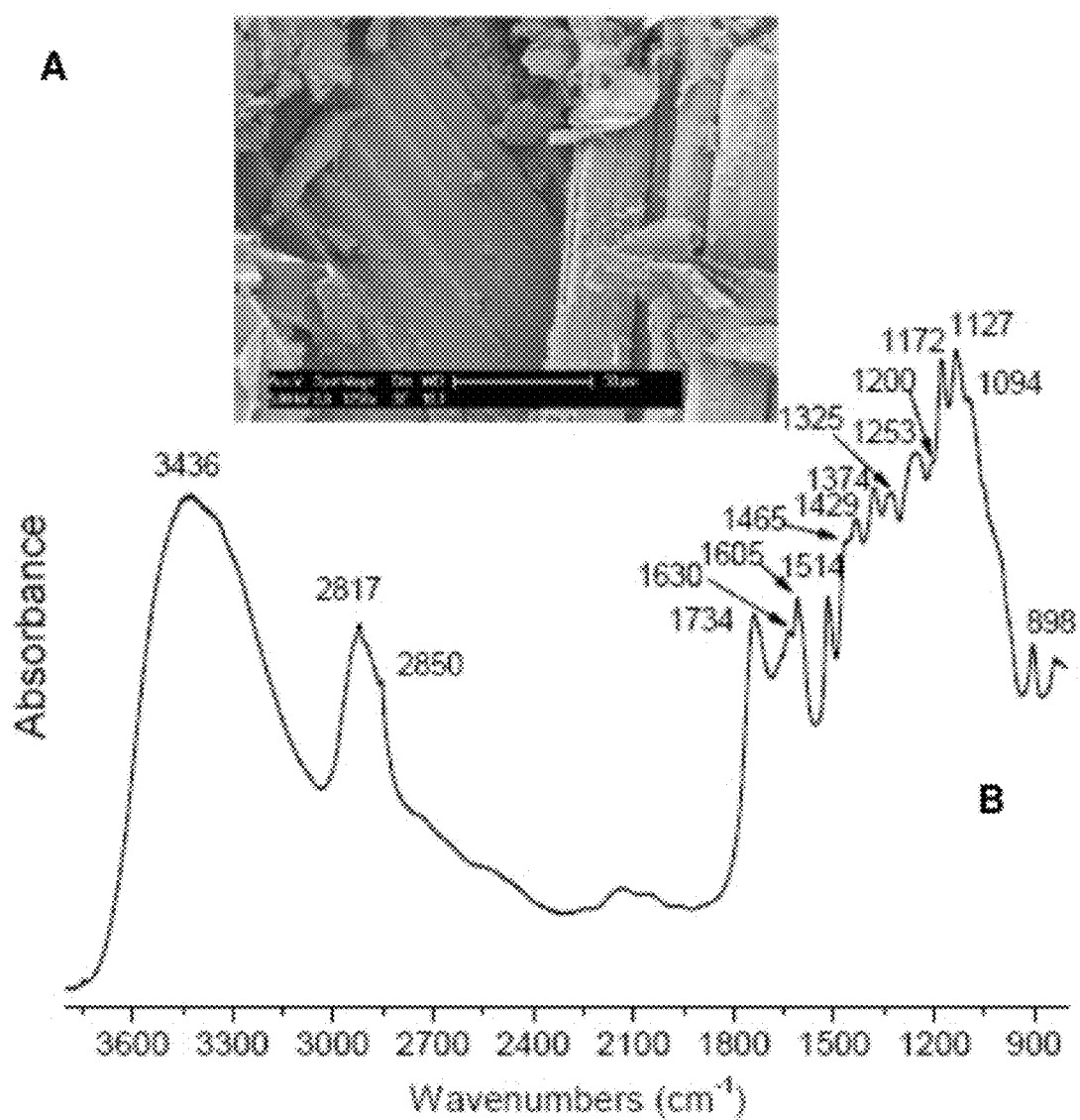
FIG. 2 is a scanning Electron Micrograph (SEM) micrograph (A) and Fourier Transform Infrared (FTIR) spectrum of raw Miscanthus (B).

FIG. 2 shows the SEM micrograph and FTIR spectrum of raw, untreated *Miscanthus*. The assignments of the characteristic absorption bands of *Miscanthus* are listed in Table 1. From the SEM images, it can be seen that the *Miscanthus* sample exhibits a smooth and rigid surface structure.

TABLE 1

Assignments of characteristic absorption bands of *Miscanthus*

| Wavenumbers (cm$^{-1}$) | Assignment |
|---|---|
| 898 | C—O—C vibrations at β-glucosidic linkages in hemicellulose and cellulose[a] |
| 1094 | C—O, C—C stretching or C—OH bending in |
| 1127 | hemicellulose and cellulose[b] |
| 1172 | C—O—C stretching at β-glucosidic linkages in |
| 1200 | cellulose and hemicellulose[c] |
| 1253 | Aromatic C—O stretching out of lignin[d] |
| 1325 | C—C and C—O skeletal vibrations[e] |
| 1374 | Aliphatic C—H vibrations[f] |
| 1429 | Aromatic C=C stretching from aromatic ring[g] |
| 1465 | Aromatic C—H vibrations[h] |
| 1514 | Aromatic C=C stretching from aromatic ring of lignin[i] |
| 1605 | Aromatic skeletal vibrations[j] |
| 1630 | Bending of Absorbed residual water[k] |
| 1734 | C=O stretching of unconjugated ketone and carboxyl group[l] |
| 2850 | |
| 2917 | C—H stretching of methyl, methylene or methane group[m] |
| 3436 | O—H stretching[n] |

[a]Sun X.F. et al., 2004; Sun et al., 2005; Oh et al., 2005; Colom and Carrillo, 2002.
[b]Xiao et al., 2001; Xu et al., 2006; Yang et al., 2007; Mascarenhas et al., 2000.
[c]Sun X.F. et al., 2004; Xu et al., 2006; Yang et al., 2007; Mascarenhas et al., 2000.
[d]Xu et al., 2006; Yang et al., 2007.
[e]Sun J.X. et al., 2004; Xu et al., 2006.
[f]Sun X.F. et al., 2004; Sun et al., 2005; Xu et al., 2006.
[g]Sun et al., 2005; Sun J.X. et al., 2004; Xu et al., 2006.
[h]Sun et al., 2005; Xu et al., 2006.
[i]Xu et al., 2006; Xu et al., 2006.
[j]Sun J.X. et al., 2004; Xu et al., 2006.
[k]Xiao et al., 2001.
[l]Sun et al., 2002; Xu et al., 2006; Sain and Panthapulakkal, 2006.
[m]Sain and Panthapulakkal, 2006; Sun et al., 1995.
[n]Sun X.F. et al., 2004; Sain and Panthapulakkal, 2006; Sun et al., 1995.

Figure 3:
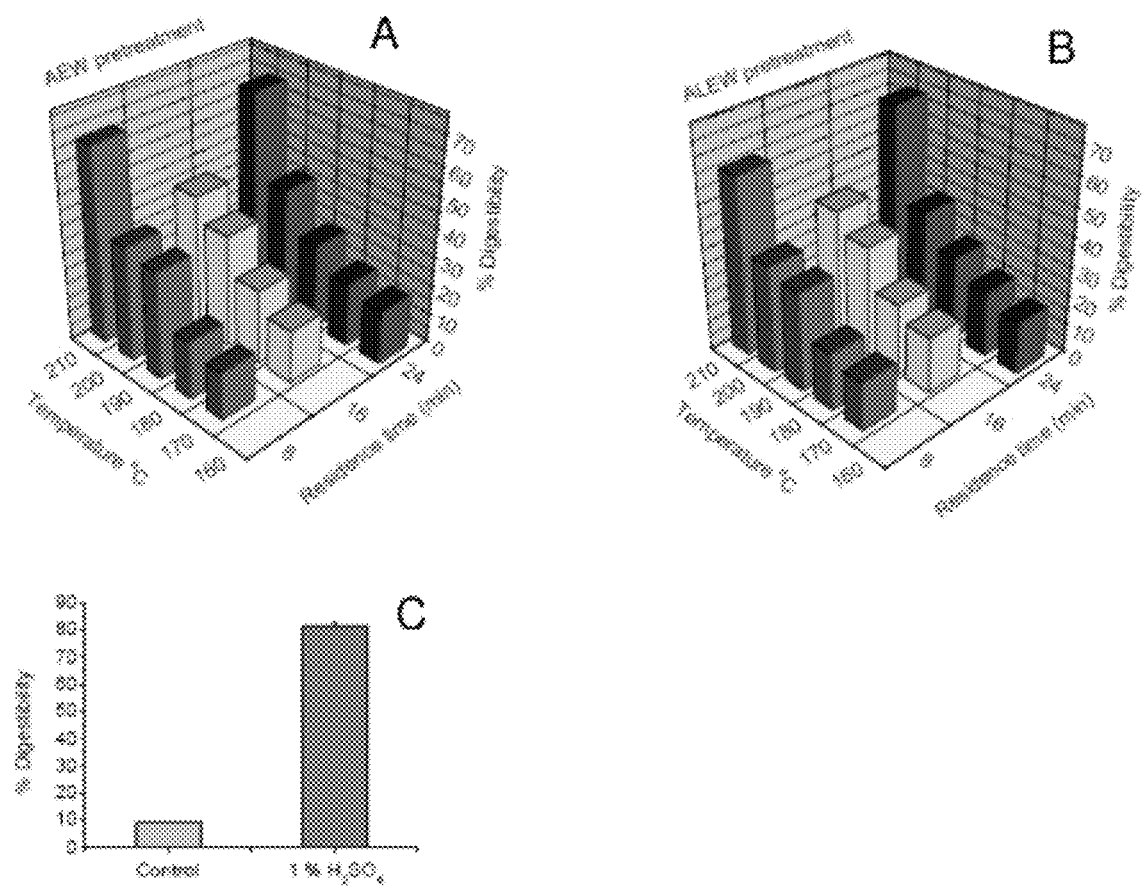
FIG. 3 shows the percent digestibility of one-step pretreated Miscanthus. (A) Acidic electrolyzed water (AEW), (B) Alkaline electrolyzed water (ALEW) and (C) Control: untreated and pretreated 1% $H_2SO_4$, 200° C., 8 min.

The percent digestibility for the one-step pretreatment is shown in FIG. 3. After a 168 hour hydrolysis, the digestibility of the AEW and ALEW pretreated *Miscanthus* (160° C., 24 min) was 18% and 17%, respectively (FIG. 3A, B). When the pretreatment temperature was increased to 190° C., a slow increase in the digestibility was observed. For the test at 200° C. for 8 min, the digestibility of the AEW and ALEW pretreated *Miscanthus* was 39% and 36%, respectively. Notably, for pretreatments with a temperature of >200° C. and a treatment time of >8 min, a rapid increase in the digestibility was observed. For the 8 min pretreatment when the temperature was >210° C., the digestibility of AEW and ALEW pretreated *Miscanthus* reached 67% and 60%, respectively. Similarly, at 200° C., when the residence time was increased to 24 min, the digestibility of AEW and ALEW pretreated *Miscanthus* became 71% and 70%. In comparison, for *Miscanthus* samples treated by 1% $H_2SO_4$ at 200° C. for 8 min, 81% cellulose was digested (FIG. 3C).

Figure 4:
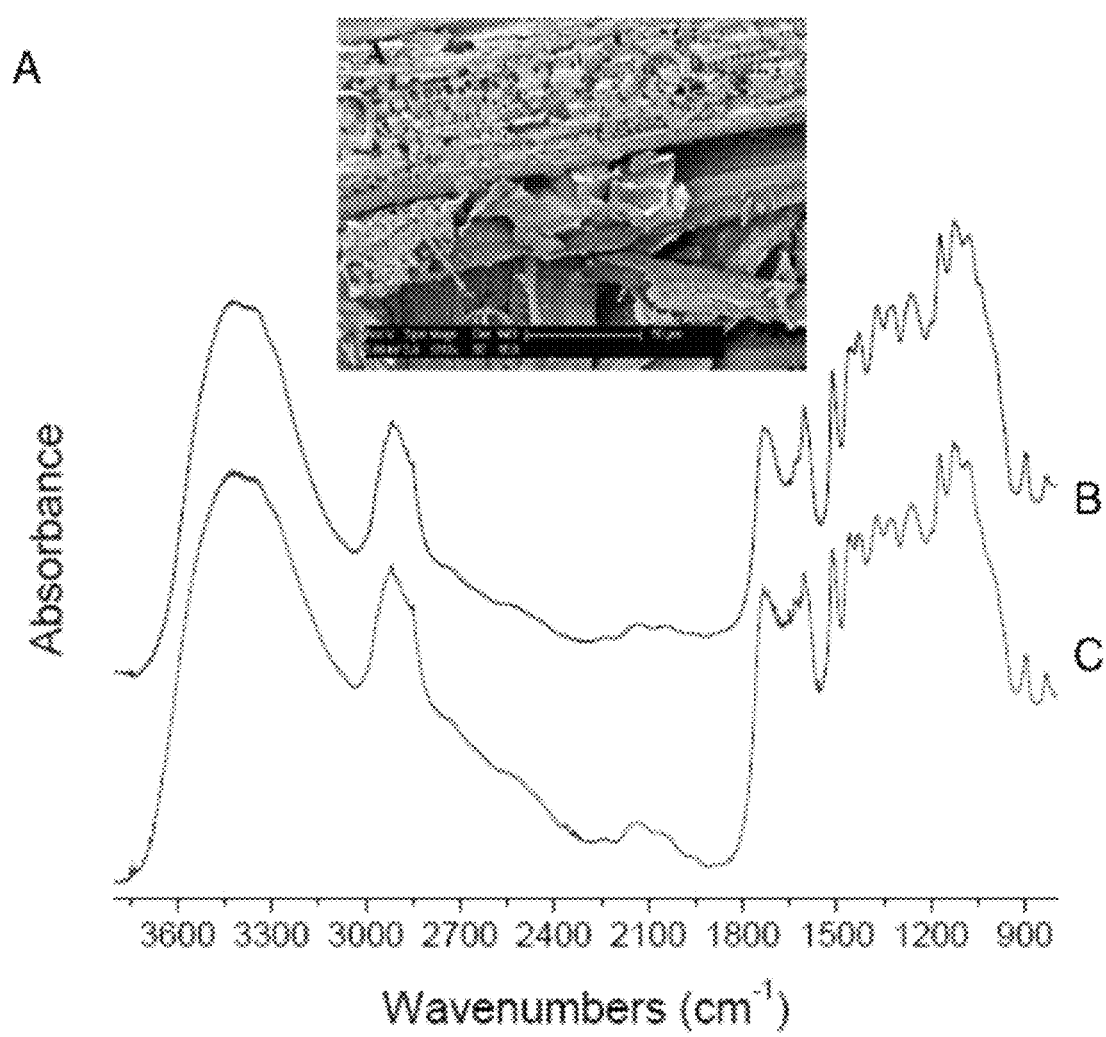
FIG. 4 shows a SEM micrograph (A) and FTIR spectra (B) of Acidic Electrolyzed Water (AEW) pretreated Miscanthus by pH 2.6 AEW (200°, 8 min) and its IITR spectra (C) after 12 hours of enzymatic hydrolysis (% digestibility=24.7±0.8)
Figure 5:
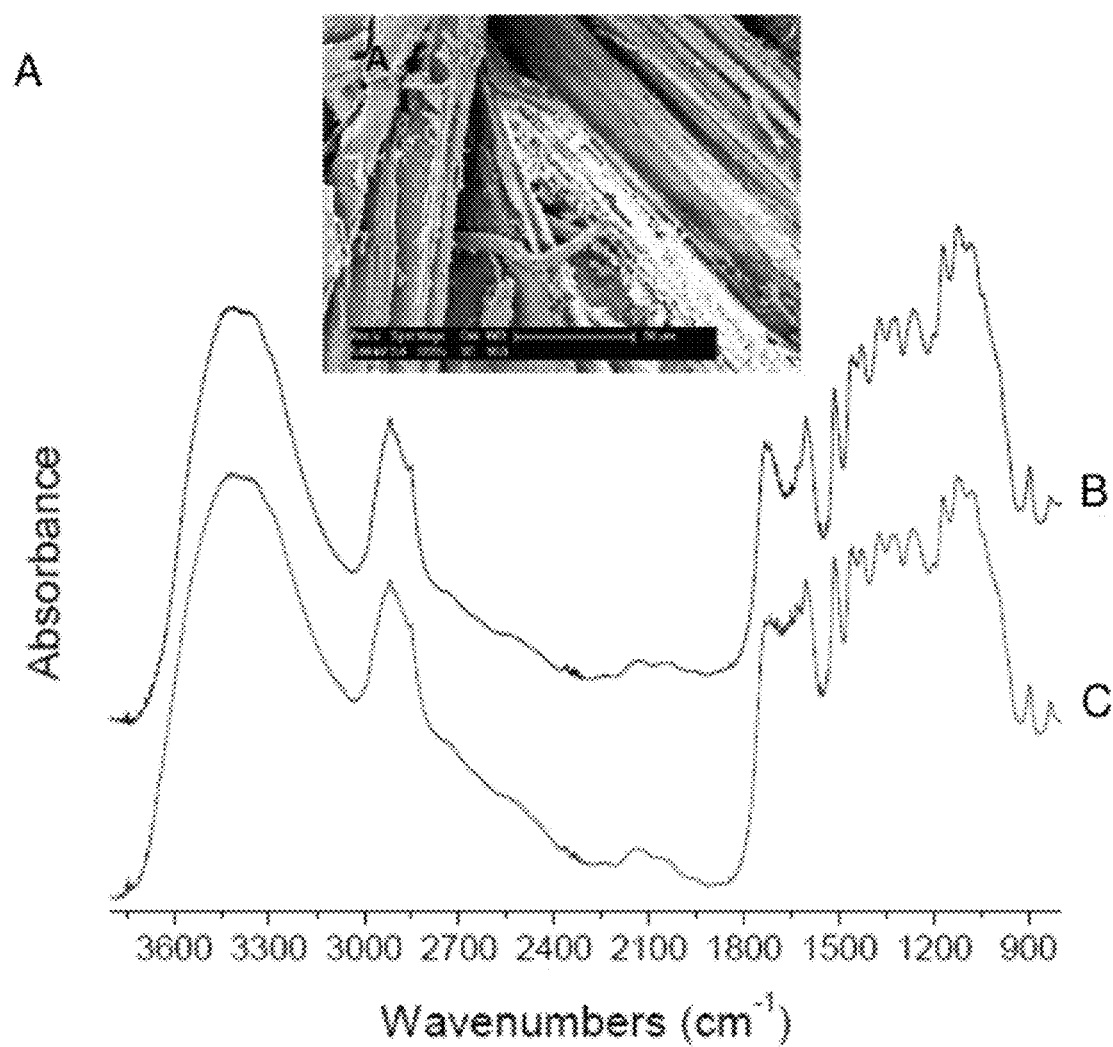
FIG. 5 shows an SEM micrograph (A) and FTIR spectra (B) of pretreated Miscanthus by pH 11.4 ALEW (200° C., 8 min) and its FTIR spectrum (C) after 12 hours of enzymatic hydrolysis (% digestibility=21.7±0.9)

A comparison of SEM images and FTIR spectra show that the AEW and ALEW pretreatments resulted in formation of pores and cracks on the surface of *Miscanthus* (FIGS. 4A and 5A), but the macroscopic structure of Miscanthus, as suggested by the FTIR spectra (FIGS. 4B and 5B), remained largely unbroken. By comparing the FTIR spectrum of AEW and ALEW pretreated *Miscanthus* (FIG. 4B, 5B) with that of untreated *Miscanthus* (FIG. 2), one can see that the peaks in Table 1 were not changed dramatically. After 12 hours of hydrolysis, the intensity of polysaccharide (hemicellulose and cellulose) peaks around 898, 1094, 1127, 1172, 1200, 1325, and 1374 cm$^{-1}$ of FIGS. 4C and 5C was lower than those of FIGS. 4B and 5B, but the lignin peaks around 1253 and 1514 cm$^{-1}$ were almost not changed. Moreover, the peak around 1734 cm$^{-1}$, corresponding to ester-linked acetyl, feruloyl and p-coumaroyl groups between hemicellulose and lignin, was lowered but still existed.

Figure 6:
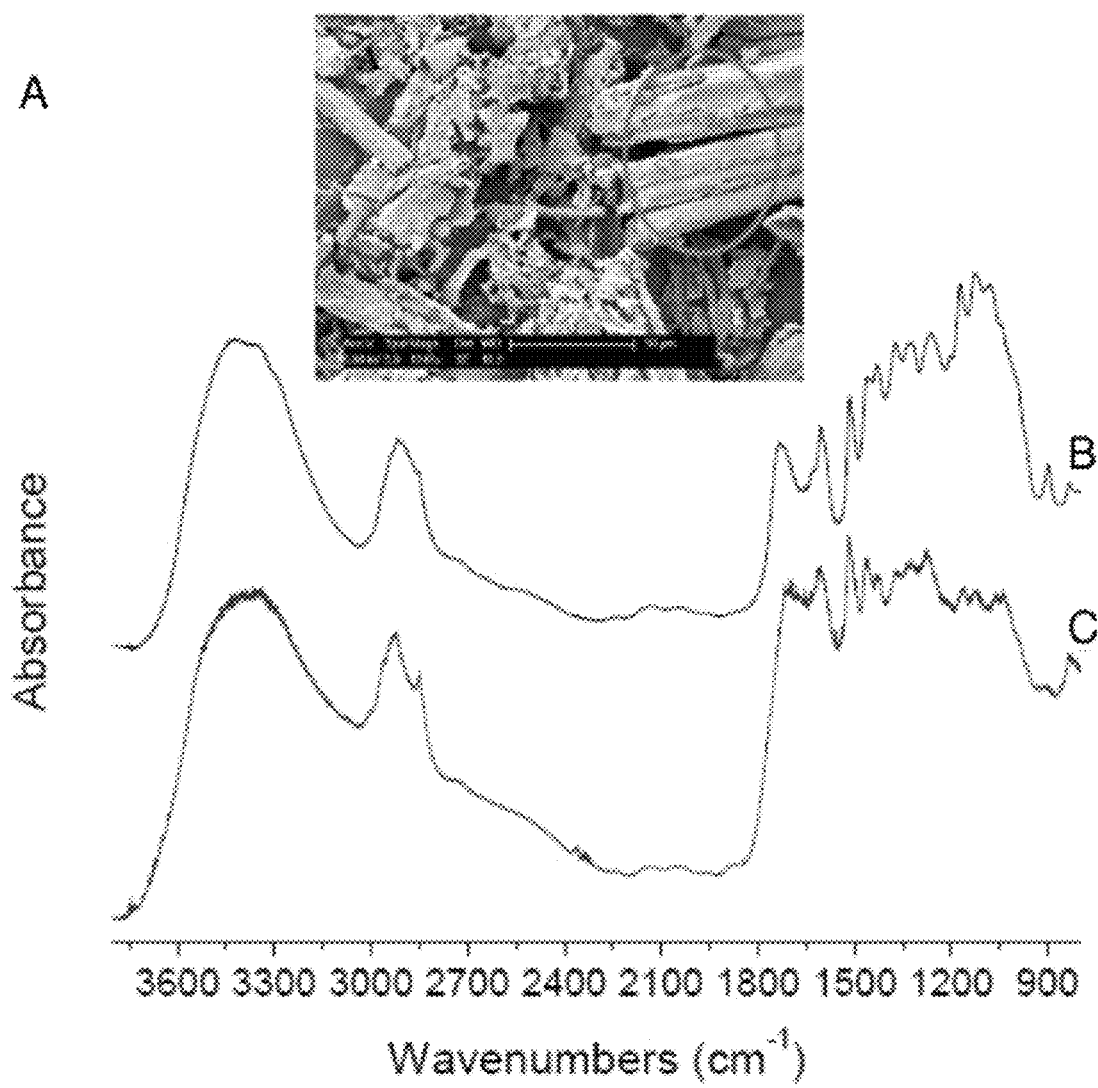
FIG. 6 shows an SEM micrograph (A) and FTIR spectra (B) of pretreated Miscanthus by 1% $H_2SO_4$ (200° C., 8 min) and its FTIR spectrum (C) after 12 hours of enzymatic hydrolysis (% digestibility=61.0±3.2). The oval in (A) highlights an unbroken region.

Compared to the electrolyzed water pretreatments, the 1% $H_2SO_4$ pretreatment alone more effectively broke down the rigid structure of *Miscanthus*. While this treatment may produce more reactive sites for enzymatic attack than either AEW or ALEW treatment, part of the sample, shown circled in FIG. 6A, remained unbroken. A close look at the FTIR spectrum of 1% $H_2SO_4$ pretreated *Miscanthus* (FIG. 6B) and that of untreated *Miscanthus* (FIG. 2B) reveals that the intensity of most polysaccharide peaks was dramatically lowered, an indication of depolymerization of polysaccharides in the catalyst solution. The peaks around 1253, 1514 and 1734 cm$^{-1}$ were still visible though with a lowered intensity. These remaining lignin and ester linkages might hinder further hydrolysis.

Effect of Two-Step Pretreatment

Figure 7:
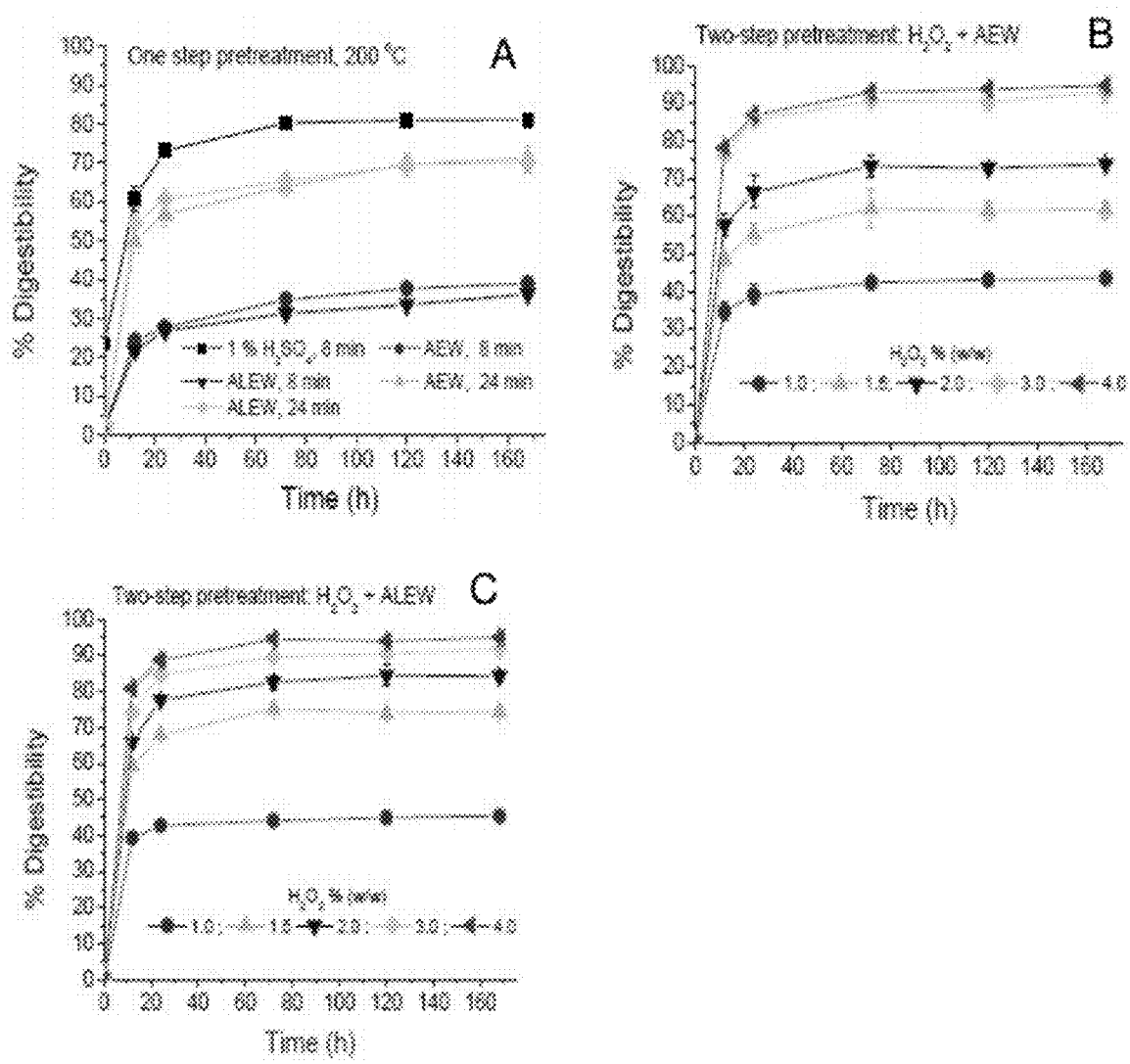
FIG. 7 shows a hydrolysis time course of one-step and two-step pretreated Miscanthus using 15 FPU/g cellulose Celluclast 1.5+Novozyme 188 mixture (1:1 v/v) at pH 5.0 at 50° C.: (A) One step pretreatment; (B) Extracting hemicellulose by alkaline $H_2O_2$ (pH 11.5, 24 hours), then treated with AEW at 121° C. for 1 hour and (C) Extracting hemicellulose by alkaline $H_2O_2$ (pH 11.5, 24 hours), then treated with ALEW at 121° C. for 1 hour

The digestibility of one-step and two-step pretreated *Miscanthus* was compared (FIG. 7). Both the hydrolysis rate and the digestibility for the two-step treated samples were higher as compared to the samples pretreated with the one-step method. In the two-step pretreated *Miscanthus* samples (FIG. 7B, 7C), a 24 hour hydrolysis digested over 85% of the cellulose. The hydrolysis appeared to reach the end point, where an increase in hydrolysis time to 72 hours did not result in additional sugar yield. However, in the one-step pretreated samples (FIG. 7A) 120 hours of hydrolysis was needed to reach the end point except for the 1% $H_2SO_4$ pretreatment (200° C., 8 min). After a 1$^{st}$ pretreatment at 50° C. by 1% alkaline peroxide, both subsequently AEW- and ALEW-pretreated (121° C., 50 min) samples had a higher sugar yield than their counterpart in the one-step pretreatment at 200° C. for 8 min.

Figure 8:
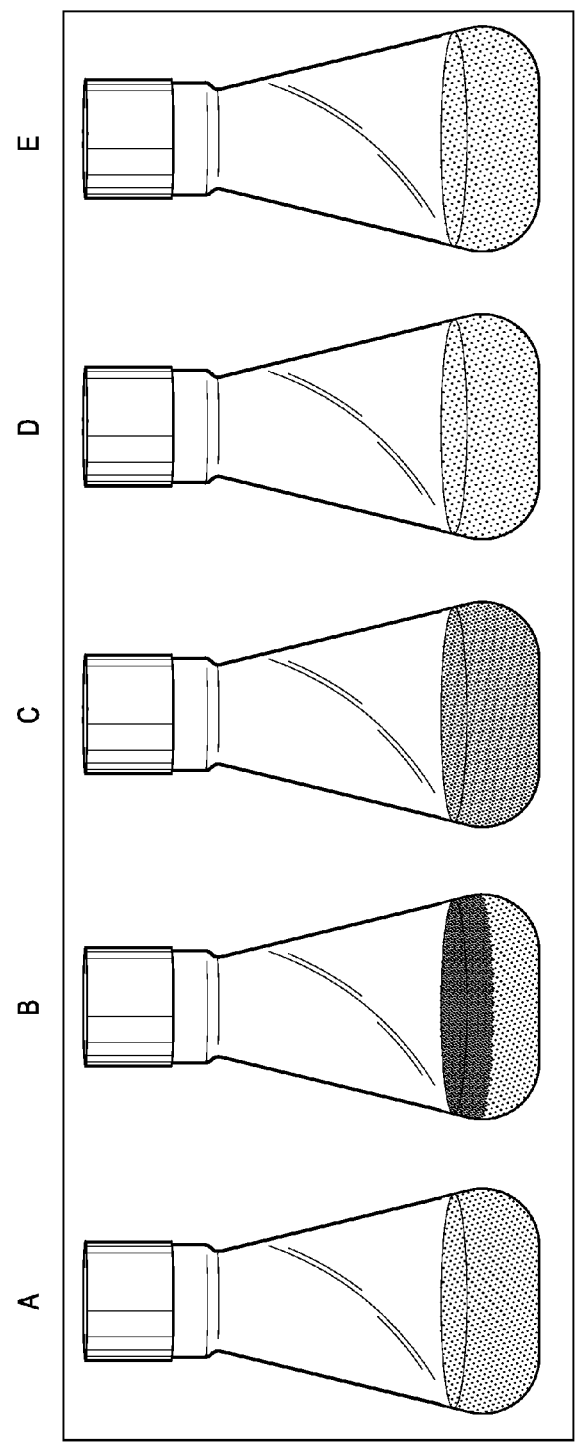
FIG. 8 shows pictures of one-step (200° C., 8 min) and two-step pretreated Miscanthus samples: (A) AEW pretreated; (B) $H_2SO_4$ pretreated; (C) ALEW pretreated; (D) Alkaline peroxide (2%, pH 11.5)+AEW pretreated (121° C., 50 min) and (E) Alkaline peroxide (2%, pH 11.5)+ALEW pretreated (121° C., 50 min)

When the concentration of peroxide was below 3%, an increase in $H_2O_2$ concentration was accompanied by a significant increase in digestibility. After the concentration of peroxide has reached 3%, increasing the $H_2O_2$ concentration did not significantly improve digestibility. When the $H_2O_2$ concentration was below 3%, the ALEW pretreatment led to significantly higher digestibility than the AEW pretreatment did. The digestibility for 2% $H_2O_2$+ALEW pretreatment (FIG. 7C) reached 84%, which was higher than that from 1% $H_2SO_4$ (200° C., 8 min) treated samples. The highest digestibility of 95% was achieved in the $H_2O_2$+ALEW two-step process after a 72 hour hydrolysis. FIG. 8 shows pictures of one-step (FIGS. 8A-C) and two-step (FIGS. 8D & E) pretreated *Miscanthus* samples (200° C., 8 min). The 1% $H_2SO_4$ (200° C., 8 min) pretreatment produced the darkest *Miscanthus* slurry indicating the generation of degradation products, followed by the AEW and ALEW pretreated (200° C., 8 min) samples (FIG. 8). The two-step pretreated *Miscanthus* slurries had a light color, from which HPLC analysis did not detect ethanol fermentation inhibitors such as furfural and HMF.

Figure 9:
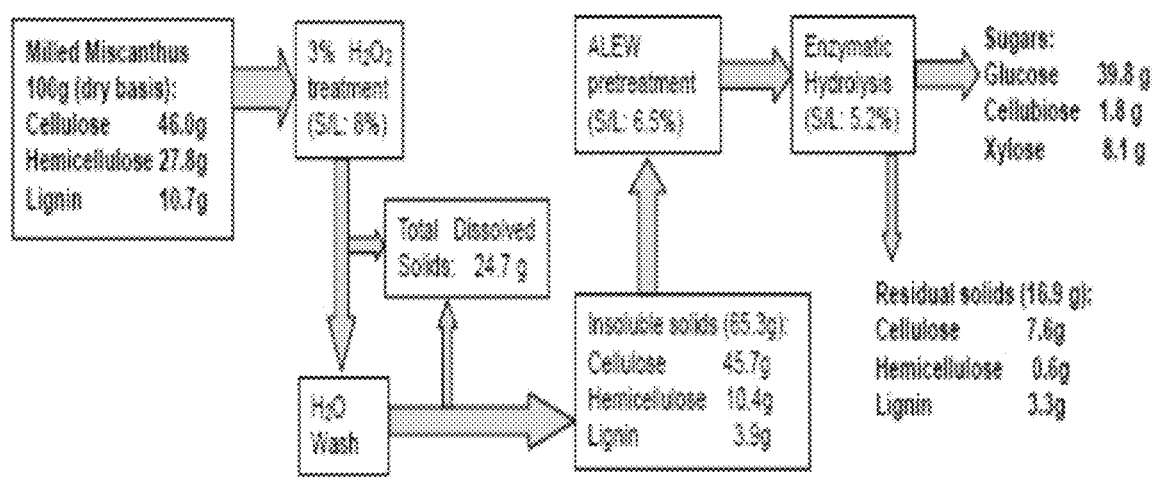
FIG. 9 shows a mass balance flow sheet of two-step pretreatment and enzymatic hydrolysis of Miscanthus.

To examine the effect of the two-stage process on the separation of hemicellulose and lignin from cellulose in the lignocellulosic biomass feedstock, a mass balance experiment was conducted (FIG. 9) using 100 g *Miscanthus*. The sample (S/L: 8%) was subjected to 3% $H_2O_2$ (pH 11.5, 50° C., 150 rpm for 24 hours) and ALEW (121° C. for 50 min) sequential pretreatments, followed by an enzymatic hydrolysis at a relatively high S/L loading ratio of 5.2%. For the specific pretreatment conditions and S/L loadings used in this test, it was found that, after the 1$^{st}$ pretreatment 63% hemicellulose and 64% lignin were removed from the recalcitrant *Miscanthus*. Cellulose was enriched from 46% to 70% in 65.3 g insoluble solids. The total percentage of polysaccharide (cellulose and hemicellulose) was increased from 74% in the untreated *Miscanthus* to 86% due to the removal of extractives. A washing step resulted in a 10% mass loss of the original *Miscanthus*. After the enzymatic hydrolysis, 84% cellulose digestion was achieved. This value is higher than that from the 1% $H_2SO_4$ (200° C., 8 min) pretreated samples hydrolyzed at a 1% S/L. It appears that after the two-step pretreatment, hemicellulose in the residual solids becomes susceptible to cellulose as suggested by the evidence that 94% hemicellulose was digested by cellulase which was thought to be ineffective at digesting hemicellulose (Dien et al., 2008). A typical composition of selected biomass is given in Table 2 (de Vrije et al., 2002; Galbe and Zacchi, 2007).

TABLE 2

Typical composition of selected biomass feedstocks

|  | Spruce | Pine | Corn stover | *Miscanthus* |
|---|---|---|---|---|
| Glucose | 45.0 | 43.3 | 36.8 | 39.5 |
| Mannose | 13.5 | 10.7 | — | — |
| Xylose | 6.6 | 5.3 | 22.2 | 19.0 |
| Arabinose | 1.2 | 1.6 | 5.5 | 1.8 |
| Galactose | 1.6 | 2.9 | 2.9 | 0.4 |
| Lignin | 27.9 | 28.3 | 23.1 | 25.0 |
| Others | 4.2 | 7.9 | 9.5 | 8.9 |

Figure 10:
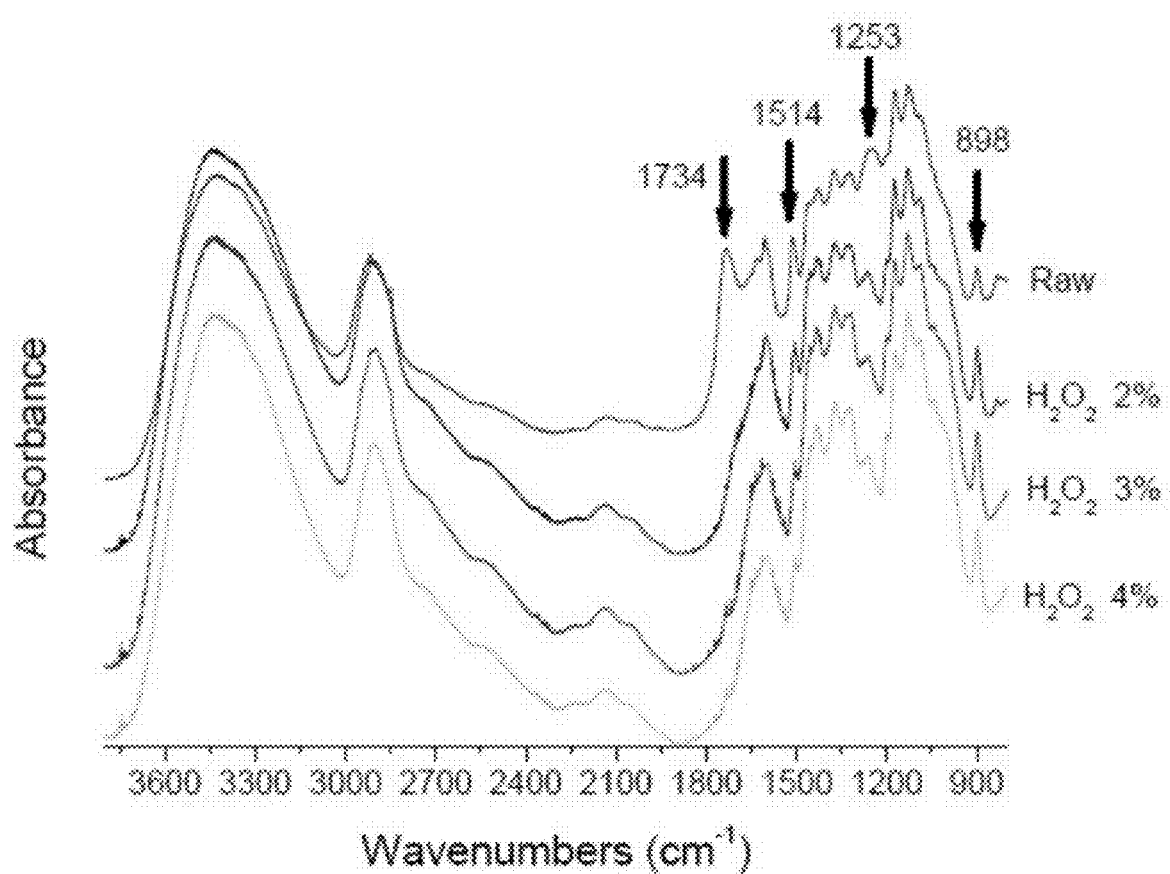
FIG. 10 shows FTIR spectra of pretreated Miscanthus with alkaline 2%, 3% and 4% $H_2O_2$ at pH 11.5, 50° C. for 24 hours.

FIG. 10 shows that after the $1^{st}$ pretreatment the lignin peaks around 1253 and 1514 $cm^{-1}$ are diminished which may be a result of a partial removal of the lignin wrapping on the surface of the cellulose. A total disappearance of 1734 $cm^{-1}$, representing breaking up of the complex linkages between hemicellulose and lignin such as ester-linked acetyl, feruloyl and p-coumaroyl groups, is a result of a decrease in hemicellulose content. It also provides an explanation on why residual hemicellulose was highly digestible during the hydrolysis. After the $1^{st}$ pretreatment, the polysaccharide peaks (898, 1094, 1127, 1172, 1200, 1325, and 1374 $cm^{-1}$) became shaper, which corresponds well to the polysaccharide content increase after the treatment.

Figure 11:
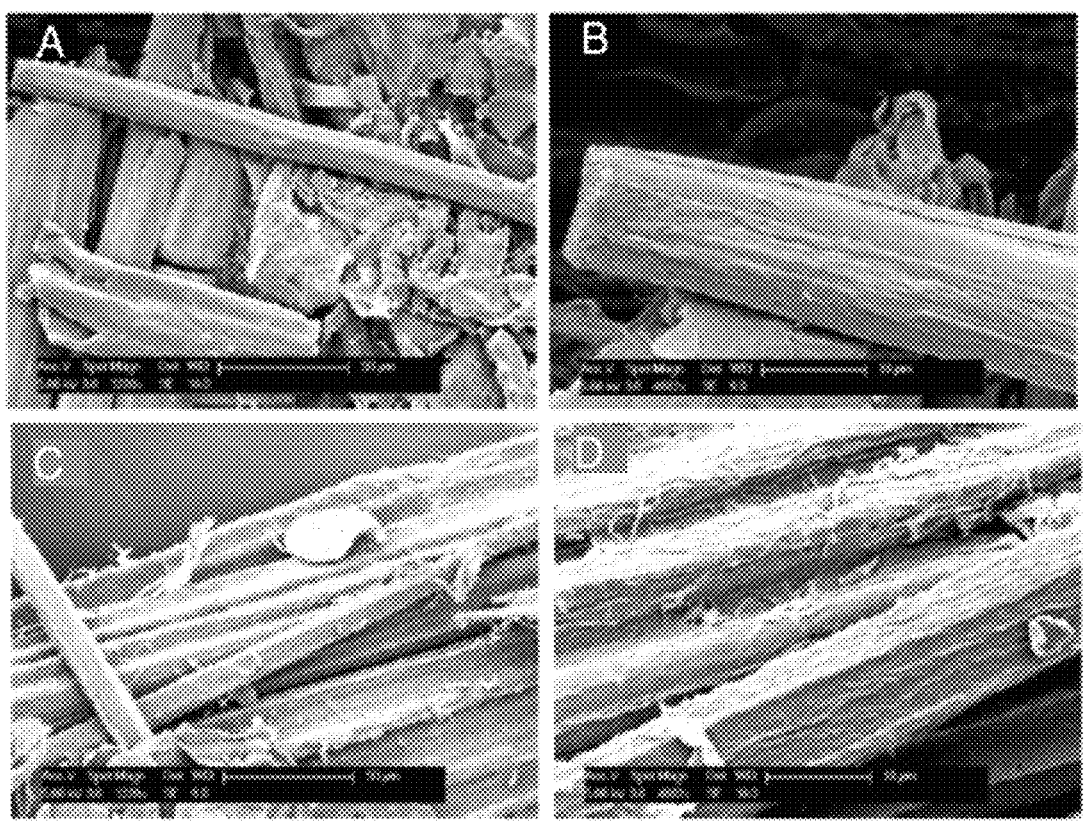
FIG. 11 shows SEM micrographs of one-step sulphuric acid ($H_2SO_4$) pretreated Miscanthus. One Step Pretreatment: SEM micrographs of pretreated Miscanthus by 3% $H_2O_2$ (pH 11.5, 50° C., 24 hours). (A) and (C) are two different spots from the same sample. (A) and (B) are the same spot at different magnifications. (C) and (D) are the same spot at different magnifications. (A) and (C) are at a magnification of 1220×; (B) and (D) are at a magnification of 4882×.
Figure 12:
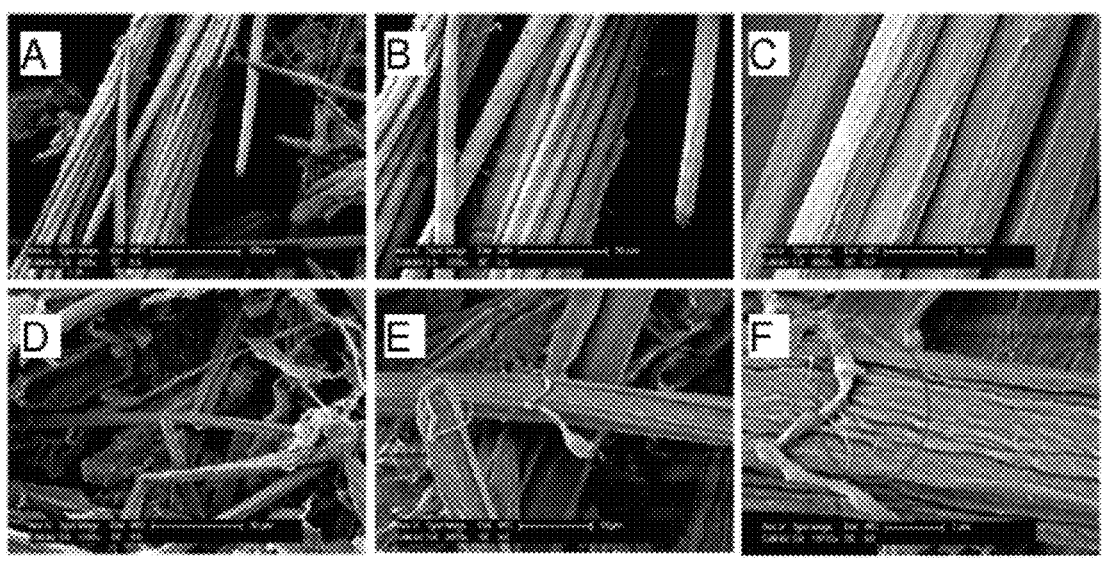
FIG. 12 shows SEM micrographs of two-step pretreated Miscanthus. Two-Step Pretreatment: SEM micrographs of pretreated Miscanthus by 3% $H_2O_2$ (pH 11.5, 50° C., 24 hours) then pretreated by AEW (top row) and ALEW (bottom row) respectively at 121° C. for 50 min. Magnification is increasing from left to right. The oval in (F) highlights a region with discernable macrofibrils.

The SEM micrographs from two different spots of pretreated *Miscanthus* are shown in FIG. 11. Compared with the SEM micrographs in FIG. 2A, one can see that, after the hemicellulose and lignin removal, the cellulose fibers appear like a skinned banana from the recalcitrant matrix. While some of the cellulose fibers were still stuck to each other, the majority of the fibers were well separated (FIGS. 11A1, 11B1 and 11B2). The diameter of the fibers was ~10 μm. It appears the AEW pretreatment (121° C., 50 min) has removed residual hemicellulose and lignin leaving behind cleaner and more exposed cellulose fibers (FIG. 12, top row). The ALEW pretreatment also further exposed cellulose fibers to the surroundings as more cracks appeared on the surfaces compared to those pretreated by AEW (FIG. 12, bottom row). As the magnification was increased to 19,715×, their sub-units and macrofibrils became discernable. The size and morphological features of cellulose fibers from *Miscanthus* observed in the tests were very similar to cellulose fibers obtained by Liu et al (2005) after they completely removed hemicellulose and lignin from wheat straw.

The results indicate *Miscanthus* is a recalcitrant energy crop that requires harsh experimental conditions (above 200° C.) to deconstruct when using conventional one-step pretreatments with 1% $H_2SO_4$, AEW (pH 2.6) or ALEW (pH 11.4). The two-stage pretreatment approach significantly enhanced cellulose digestibility and shortened enzymatic hydrolysis time. The highest digestibility of 95% was achieved using an alkaline peroxide and ALEW sequential pretreatment. From the SEM observations, after the $1^{st}$ pretreatment cellulose fibers were exposed to surroundings so that the $2^{nd}$ pretreatment could be conduced at a mild temperature of 121° C. The reduced pretreatment temperature minimizes sugar losses and the formation of inhibitory products. In addition, the disruption of the linkages between hemicellulose and lignin, as shown by the FTIR curves, renders the residual hemicellulose highly digestible to cellulase.

Example 3

Fermentation without Detoxification

The *Miscanthus* hydrolysate produced with the two-stage method was fermented with Baker yeast at 30° C. No detoxification was used before fermentation. The hydrolysate was however enriched with the formula given in Table 3. A control with glucose added in the fermentation medium was also conducted. The volume of fermentation medium was 70 ml/flask. 0.2 ml activated seed culture was added in 70 ml fermentation medium. After and during fermentation, the concentration of glucose and ethanol was analyzed by HPLC.

TABLE 3

Fermentation medium.

|  |  | Fermentation Medium | |
|---|---|---|---|
| | Ingredients | Control | Hydrolysate medium |
| Nutrient | 1 g/L Yeast Extract | + | + |
|  | 30 g/L Glucose | + |  |
|  | 0.5 g/L $(NH_4)_2HPO_4$ | + | + |
|  | 0.025 g/L $MgSO_4 \cdot 7H_2O$ | + | + |
|  | 1.38 g/L $NaH_2PO_4$ | + | + |
|  | Hydrolysate |  | + |

Results:

The fermentation results are summarized in Table 4. It can be seen that, the hydrolysate exhibited good fermentability, comparable to that of the control. It is an indication that the inhibitory compounds production in the two-stage process is minimal and the hydrolysate can be directly used for fermentation without going through a detoxification process. The detoxification process will add cost to the bio-ethanol production process, due to added equipment cost, energy consumption, and sugar losses during detoxification.

TABLE 4

Fermentation of *Miscanthus* hydrolysate enriched with nutrients

| Time | Control | | Hydrolysate | |
|---|---|---|---|---|
| (hour) | Glucose (g/L) | Ethanol (g/L) | Glucose (g/L) | Ethanol (g/L) |
| 0 | 18.42 | 0.00 | 15.48 | 0.00 |
| 12 | 0.00 | 7.10 | 0.00 | 9.31 |
| 24 | 0.00 | 8.44 | 0.00 | 8.14 |
| 48 | 0.00 | 8.62 | 0.00 | 8.88 |
| 72 | 0.00 | 7.64 | 0.00 | 7.53 |

Example 4

Fermentation *Miscanthus* Hydrolysate without Nutrients Enrichment

The *Miscanthus* hydrolysate produced with the two-stage method was fermented with Baker yeast at 30° C. with the same conditions used in Example 3. In this test, no nutrients were added in the fermentation of hydrolysate. But for the control, the same nutrient was used as can be seen in Table 5.

TABLE 5

Nutrient used in the Control.

| | | Fermentation Medium | |
|---|---|---|---|
| | Ingredients | Control | Hydrolysate medium |
| Nutrient | 1 g/L Yeast Extract | + | |
| | 30 g/L Glucose | + | |
| | 0.5 g/L $(NH_4)_2HPO_4$ | + | |
| | 0.025 g/L $MgSO_4 \cdot 7H_2O$ | + | |
| | 1.38 g/L $NaH_2PO_4$ | + | |
| | Hydrolysate | | + |

Results:

Similarly, the fermentation of hydrolysate from *Miscanthus* treated with the 2-stage method was successful even though no nutrients were added (See Table 6). It demonstrated that the hydrolysate from *Miscanthus* treated with the 2-stage pretreatment can be directly used for ethanol fermentation without detoxification and addition of additional nutrients.

TABLE 6

Ethanol yield in *Miscanthus* hydrolysate fermentation.

| Time | Control | | Hydrolysate | |
|---|---|---|---|---|
| (hour) | Glucose (g/L) | Ethanol (g/L) | Glucose (g/L) | Ethanol (g/L) |
| 0 | 31.97 | 0.15 | 21.63 | 0.05 |
| 12 | 14.51 | 9.56 | 14.88 | 6.23 |
| 24 | 1.61 | 13.96 | 10.67 | 7.31 |
| 48 | 0.06 | 14.69 | 4.24 | 10.02 |
| 72 | 0.06 | 14.80 | 0.06 | 11.35 |

Example 5

Hemicellulose Separation

In the two-stage method, the stage one treatment with $H_2O_2$ is aimed at removing hemicellulose and lignin for value-added products production. To examine the recovery of hemicellulose from the liquid portion after the 1st pretreatment, an experiment was designed and conducted. 10 g (dry weight) switchgrass, which had a composition of 32.02% glucan, 20.2% xylan and 17.25% lignin, was first mixed with an alkaline peroxide solution (concentration of 1%, 2%, and 3% w/w) at pH 11.5 in 500 mL Erlenmeyer flasks. The solid loading was brought to 5% w/w. The experiments were carried at 50° C. and at 150 rpm for different treating times (16 h and 24 h) in a Classice C76 water bath shaker (New Brunswick Scientific, New Brunswick, N.J.).

After extraction, the slurries were centrifuged and the supernatants were removed. Using 50% (v/v) acetic acid, the pH of the supernatants was adjusted to 5.0. As the pH decreased, the solution became cloudy, and then was put into refrigerator at 4° C. for 24 h. After that, the hemi-cellulose A precipitated and was removed by centrifugation. After the precipitation of hemi-cellulose A, the left liquid was mixed with 3-volume 95% ethanol, and then hemicellulose B was separated immediately by centrifugation.

The hemicellulose A and hemicellulose B solids (See FIG. 1) were put into conventional oven for drying at 60° C. till the weight was constant. The hemicellulose yields are shown in Table 7.

TABLE 7

Hemicellulose recovery from switchgrass treated with the two-stage method.

| (g) | 16 h | 24 h |
|---|---|---|
| 1% $H_2O_2$ loading | | |
| Hemicellulose A | 0.14 | 0.16 |
| Hemicellulose B | 0.97 | 1.22 |
| Total hemicellulose | 1.11 | 1.38 |
| 2% $H_2O_2$ loading | | |
| Hemicellulose A | 0.7 | 1.04 |
| Hemicellulose B | 1.44 | 1.78 |
| Total hemicellulose | 2.14 | 2.82 |
| 3% $H_2O_2$ loading | | |
| Hemicellulose A | 0.27 | 0.72 |
| Hemicellulose B | 1.54 | 1.70 |
| Total hemicellulose | 1.81 | 2.42 |

The two-stage fractionation process of lignocellulosic biomass disclosed herein provides an improved platform for the production of biofuels and other value-added products from feedstocks that minimizes the current weaknesses of biomass deconstruction methods.

REFERENCES

Blake J D, Murphy P T, Richards G N. 1971. Isolation and A/B classification of hemicelluloses. Carbohyd Res 16:49-57.

Crittenden R G, Playne M J. 1996. Production, properties and applications of food-grade oligosaccharides. Trends in Food Sci Technol 7:353-360.

Cuissinat C, Navard P. 2006a. Swelling and dissolution of cellulose Part I: free floating cotton and wood fibres in N-Methylmorpholine-N-Oxide-Water Mixtures. Macromol Symp 244: 1-18.

Dadi A P, Schall C A, Varanasi S. 2007. Mitigation of cellulose recalcitrance to enzymatic hydrolysis by ionic liquid pretreatment. Appl Biochem Biotechnol 136-140:407-421

Dadi A P, Varanasi S, Schall C A. 2006. Enhancement of cellulose saccharification kinetics using an ionic liquid pretreatment step. Biotechnol Bioeng 95(5):904-910.

de Vrije T, de Haas G G, Tan G B, Keijsers E R P, Claassen P A M. 2002. Pretreatment of Miscanthus for hydrogen production by *Thermotoga elfii*. Int J Hydrogen Energy 27: 11-12.

Dien B S, Ximenes E A, O'Bryan P J, Moniruzzaman M, Li X, Balan V, Dale B, Cotta, M. 2008.

Enzyme characterization for hydrolysis of AFEX and liquid hot-water pretreated distillers' grains and their conversion to ethanol. Bioresour Technol 99:5216-5225.

Doner L W, Chau H K, Fishman M L, Hicks, K. 1998. An improved process for isolation of corn fiber gum. Cereal Chem 75:408-411.

Doner L W, Johnston D B, Singh V. 2001. Analysis and properties of arabinoxylans from discrete corn wet-milling fiber fractions. J Agric Food Chem 49:1266-1269.

Doner L W, Hicks K B. 1997. Isolation of hemicellulose from corn fiber by alkaline hydrogen peroxide extraction. Cereal Chem 74(2):176-181

Eggeman T, Elander R T. 2005. Process and economic analysis of pretreatment technologies. Bioresource Technol 96(18):2019-2025.

Fang J M, Sun R C, Tomkinson J. 2000. Isolation and characterization of hemicelluloses and cellulose from rye straw by alkaline peroxide extraction. Cellulose 7:87-107.

Galbe M, Zacchi G. 2007. Pretreatment of lignocellulosic materials for efficient bioethanol production. Adv Biochem Engi/Biotechnol 108: 41-65.

Hahn-Hägerdal B, Galbe M, Gorwa-Grauslund M F, Udell Zacchi G. 2006. Bio-ethanol—the fuel of tomorrow from the residues of today. Trends Biotechnol 24(12):549-556.

Hromadkova Z, Ebringerova A. 1995. Isolation and characterization of hemicelluloses from corn hulls. Chem Papers 49:97-101.

Jones M, Walsh M. 1990. *Miscanthus* for energy and fiber. London: James & James Ltd. Preface.

Kamm B, Kamm M. 2004. Principles of biorefineries. App Microbiol Biotechnol 64:137-145.

Kim K H, Hong J. 2001. Supercritical CO2 pretreatment of lignocellulose enhances enzymatic cellulose hydrolysis. Bioresour Technol 77(2):139-44.

Kim C, Hung Yen-Con B, Robert E. 2000. Roles of Oxidation-Reduction Potential in electrolyzed oxidizing and chemically modified water for the Inactivation of food-related pathogens. J Food Prot 63:19-24.

Kim S, Holtzapple M T. 2005. Lime pretreatment and enzymatic hydrolysis of corn stover, Bioresource Technol 96(18):1994-2006.

Kim T H, Lee Y Y. 2005. Pretreatment and fractionation of corn stover by ammonia recycle percolation process. Bioresource Technol 96(18):2007-2013.

Koga K, Fujikawa S. 1993. Japanese Technology Reviews. Section E Biotechnology, Xyloologosaccharide 130-143.

Kosan B, Michels C, Meister F. 2008. Dissolution and forming of cellulose with ionic liquids. Cellulose 15: 59-66.

Liu C, Wyman C E. 2005. Partial flow of compressed-hot water through corn stover to enhance hemicellulose sugar recovery and enzymatic digestibility of cellulose. Bioresource Technol 96(18): 1978-1985.

Liu R, Yu H, Huang Y. 2005. Structure and morphology of cellulose in wheat straw. Cellulose 12: 25-34.

Lloyd T A, Wyman C E. 2005. Combined sugar yields for dilute sulphuric acid pretreatment of corn stover followed by enzymatic hydrolysis of the remaining solids. Bioresource Technol 96(18):1967-1977.

Mascarenhas M, Dighton J, Arbuckle G A. 2000. Characterization of plant carbohydrates and changes in leaf carbohydrate chemistry due to chemical and enzymatic degradation measure by microscopic ATR FT-IR spectroscopy. Appl Spectrosc 54:681-686.

Mosier N, Hendrickson R, Ho N, Sedlak M, Ladisch M R. 2005a. Optimization of pH controlled liquid hot water pretreatment of corn stover. Bioresource Technol 96(18): 1986-1993.

Mosier N, Wyman C, Dale B E, Elander, R, Lee Y Y, Holtzapple M, Ladisch M. 2005b. Features of promising technologies for pretreatment of lignocellulosic biomass. Bioresource Technol 96(6):673-686.

Moure A, Gullón, Domínguez H, Parajó J C. 2006. Advances in the manufacture, purification and applications of xylooligosaccharides as food additives and nutraceuticals. Process Biochem 41:1913-1923.

Murnen H K, Balan V, Chundawat S P S, Bals B, Sousa L D C S, Dale B E. 2007. Optimization of ammonia fiber expansion (AFEX) pretreatment and enzymatic hydrolysis of *Miscanthus*× giganteous to fermentable sugars. Biotechnol Prog 23:846-850.

Murugesan S, Linhardt R J. 2005. Ionic liquids in carbohydrate chemistry-current trends and future directions. Current Organic Synthesis 2:437-451.

Nabarlatz D, Farriol X, Montane D. 2004. Kinetic modelling of the autohydrolysis of lignocellulosic biomass for the reduction of hemicellulose-derived oligosaccharides. Ind Eng Chem Res 43:4124-4131.

Nakata T, Miyafuji H, Saka S. 2006. Bioethanol from cellulose with supercritical water treatment followed by enzymatic hydrolysis. Appl Biochem Biotechnol 129-132:476-484.

Oh S Y, Yoo D I, Shin Y, Kim, H W, Kim H Y, Chung Y S, Park W H, Youk J H. 2005. Crystalline structure analysis of cellulose treated with sodium hydroxide and carbon dioxide by means of X-ray diffraction and FTIR spectroscopy. Carbohydr Res 340:2376-2391.

Öhgren K, Galbe M, Zacchi G. 2005. Optimization of steam pretreatment of $SO_2$-impregenated corn stover for fuel ethanol production. Appl Biochem Biotechnol 121-124: 1055-1067.

Öhgren K, Bura R, Saddler J, Zacchi G. 2007. Effect of hemicellulose and lignin removal on enzymatic hydrolysis of steam pretreated corn stover. Bioresource Technology. 98:2503-2510.

Oliva J M, Sáez R, Ballesteros I, Gonzalez A, Negro M J, Manzanares P, Ballesteros M. 2003. Effect of lignocellulosic degradation compounds from steam explosion pretreatment on ethanol fermentation by thermotolerant yeast *Kluyveromyces marxianus*. Appl Biochem Biotechnol 105-108:141-153.

Pääkkö M, Ankerfors M, Kosonen H, Nykänen Ahola S, Österberg M, Ruokolainen J, Lain J, Larsson P T, Lkkala O, Linström T. 2007. Enzymatic hydrolysis combined with mechanical shearing and high-pressure homogenization for nanoscale cellulose fibrils and strong gels. Biomacromolecules 8:1934-1941.

Palmarola-Adrados B, Galbe M, Zacchi, G. 2004. Combined steam pretreatment and enzymatic hydrolysis of starch-free wheat fibers. Appl. Biochem. Biotechnol 113-116: 989-1002.

Palonen H, Thomsen A B, Tenkanen M, Schmidt A S, Viikari L. 2004. Evaluation of wet oxidation pretreatment for enzymatic hydrolysis of softwood. Appl Biochem Biotechnol 117:1-17.

Xiang Q, Lee Y Y, Torget R W. 2004. Kinetics of glucose decomposition during dilute-acid hydrolysis of lignocellulosic biomass. Appl Biochem Biotechnol 113-116: 1127-1139.

Qian X, Nimlos M R, Johnson D K, Himmel M E. 2005. Acidic sugar degradation pathways. Appl Biochem Biotechnol 121-124:989-997.

Ragauskas A J, Williams C K, Davison B H, Britovsek G, Cairney J, Eckert C A, Frederick W J Jr, Hallett J P, Leak D J, Liotta C L, Mielenz J R, Murphy R, Templer R, Tschaplinski T. 2006. The path forward for biofuels and biomaterials. Science 311:484-489.

Roberfroid M B. 1999. Concepts in functional foods: the case of insulin and oligofructose. J Nutr 129: 398S-1401S.

Roberfroid M B, Delzenne N. 1998. Dietary fructans. Annu Rev Nutr 18:117-143.

Saha B C, Cotta M A. 2006. Ethanol production from alkaline peroxide pretreated enzymatically saccharified wheat straw. Biotechnol Prog 22:449-453.

Sain M, Panthapulakkal S. 2006. Bioprocess preparation of wheat straw fibers and their characterization. Ind Crop Prod 23:1-8.

Sassner P, Galbe M, Zacchi G. 2005. Steam pretreatment of salix with and without SO2 impregnation for production of bioethanol. Appl Biochem Biotechnol 121-124: 1101-1117.

Scheppach W, Luehrs H, T Menzel. 2001. Beneficial effects of low-digestible carbohydrate consumption. Br J Nutr 85:S23-S30.

Söderström J, Galbe M, Zacchi G. 2004. Effect of washing on yield in one- and two-step Steam pretreatment of softwood for production of ethanol. Biotechnol Prog 20:744-749.

Somerville C, Bauer S, Brininstool G, Facette M, Hamann T, Milne J, Osborne E, Paredez A, Persson S, Raab T, Vorwerk S, Youngs H. 2004. Toward a systems approach to understanding plant cell walls. Science 306:2206-2211.

Sun J X, Sun X F, Zhao H, Sun R C. 2004. Isolation and characterization of cellulose from sugarcane bagasse. Polym Degrad Stab 84:331-339.

Sun R, Lawther J M, Banks W B. 1995. Influence of alkaline pretreatments on the cell wall components of wheat straw. Ind Crop Prod 4:127-145.

Sun R C, Sun X F, Liu G Q, Fowler P, Tomkinson J. 2002. Structural and physicochemical characterization of hemicelluloses isolated by alkaline peroxide from barley straw. Poly Int 51:117-124.

Sun R C, Tomkinson J, Ma P L, Liang S F. 2000 b. Comparative study of hemicelluloses from rice straw by alkali and hydrogen peroxide treatments. Carbohydr Polym 42:111-122.

Sun R C, Tomkinson J, Mao F C, Sun X F. 2000 c. Physiochemical characterization of lignins from rice straw hydrogen peroxide treatment. J Appl Polym Sci 79:719-732.

Sun R C, Tomkinson J, Wang S, Zhu W. 2000 d. Characterization of lignins from wheat straw by alkaline peroxide treatment. Polym Degrad Stab 67:101-109.

Sun R C, Tomkinson J, Wang Y X, Xiao B. 2000 a. Physicochemical and structural characterization of hemicelluloses from wheat straw by alkaline peroxide extraction. Polymer 41:2647-2656.

Sun X F, Sun R C, Fowler P, Baird M S. 2004. Isolation and characterization of cellulose obtained by a two-stage treatment with organosolv and cynamide activated hydrogen peroxide from wheat straw. Carbohydr Polym 55:379-391.

Sun X F, Sun R C, Fowler P, Baird M S. 2005. Characteristics of degraded cellulose obtained from steam-exploded wheat straw. Carbohydr Res 340:97-106

Teymouri F, Laureano-Perez L, Alizadeh H, Dale B. 2005. Optimization of the ammonia fiber explosion (AFEX) treatment parameters for enzymatic hydrolysis of corn stover. Bioresource Technol 96(18):2014-2018.

Usuki C, Kimura Y, Adachi S. 2008. Degradation of pentoses and hexouronic acids in subcritical water. Chem Eng Technol 31(1):133-137.

Varga E, Réczey K, Zacchi G. 2004. Optimization of steam pretreatment of corn stover to enhance enzymatic digestibility. Appl Biochem Biotechnol 113-116:509-523.

Vazquez M J, Alonso J L, Domínguez H, Parajó J C. 2000. Xylooligosaccharides: manufacture and applications. Trends in Food Sci Technol 11:387-393.

Vázquez M J, Garrote G, Alonso J L, Domínguez H, Parajó J C. 2005. Refining of antohydrolysis liquors for manufacturing xylooligosaccharides: evaluation of operational strategies. Bioresource Technol 96:889-896.

Vrije T D, Haas G G D, Tan G B, Keijseers E R P, Claassen P A M. 2002. Pretreatment of *Miscanthus* for hydrogen production by *Thermotoga elfii*. Int J Hydrogen Energy 27:1381-1390.

Wyman C E, Dale B E, Elander R T, Holtzapple M M, Ladisch M R, Lee Y Y. 2005. Coordinated development of leading biomass pretreatment. Bioresource Technol 96(18):1959-1966.

Wyman C E. 2007. What is (and is not) vital to advancing cellulosic ethanol. Trends Biotechnol 25: 153-157.

Xiao B, Sun X F, Sun R C. 2001. Chemical, structural and thermal characterization of alkali-soluble lignins and hemicelluloses, and cellulose from maize stems, rye straw, and rice straw. Polym Degrad Stab 74:307-319.

Xu F, Liu C F, Geng Z C, Sun J X, Sun R C, Hei B H, Lin L, Wu S B, Je J. 2006. Characterisation of degraded organosolv hemicellulose from wheat straw. Polym Degrad Stab 91:1880-1886.

Xu F, Sun J, Sun R, Fowler P, Baird M S. 2006. Comparative study of organosolv lignins from wheat straw. Ind Crop Prod 23:180-193.

Yang B, Wyman C E. 2004. Effect of xylan and lignin removal by batch and flowthrough pretreatment on the enzymatic digestibility of corn stove cellulose. Biotechnol Bioeng 86(1):88-95.

Yang B, Wyman C E. 2008. Pretreatment: the key to unlocking low-cost cellulosic ethanol. Biofuels Bioprod Bioref 2:26-40.

Yang R, Zhang C, Feng H, Yang W. 2006. A kinetic study of xylan solubilization and degradation during corncob steaming. Biosystems Eng 93:375-382.

Yuan Q P, Zhang H, Qian Z M, Yang X J. 2004, Pilot-plant production of xylo-oligosaccharides from corncob by steaming, enzyme hydrolysis and nanofiltration. J Chem Technol Biotechnol 79:1073-1079.

Zaldivar J, Ingram L O. 1999. Effect of organic acids on the growth and fermentation of ethanologenic *Escherichia coli* LY01. Biotechnol Bioeng 66:203-210.

Zhang Y P. 2007. Cellulose-solvent-based lignocellulose fractionation with modest reaction conditions and reagent cycling. International Patent Pub No WO/2007/111605.

Zhang H, Wu J, Zhang J, He J. 2005. 1-Allyl-3-methylimidazolium chloride room temperature ionic liquid: a new and powerful nonderivatizing solvent for cellulose. Macromolecules 38(20):8272-8277.

Zhang Y P, Cui J, Lynd L R, Kuang L R. 2006. A transition from cellulose swelling to cellulose dissolution by o-phosphoric acid: evidence from enzymatic hydrolysis and supramolecular structure. Biomacromolecules 7(2):644-648.

Zhang Y P. 2008. Reviving the carbohydrate economy via multi-product lignocellulose biorefineries. J Ind Microbiol Biotechnol 35:367-375.

Zhang Y P, Ding S, Mielenz J R, Cui J, Elander R T, Laser M, Himmel M E, McMillan J R, Lynd L R. 2007. Fractionating recalcitrant lignocellulose at modest reaction conditions. Biotechnol Bioeng 97(2):214-223.

Zhu Y, Kim T H, Lee R C, Elander R T. 2006. Enzymatic production of xylooligosaccharides from corn stover and corn cobs treated with aqueous ammonia. Appl Biochem Biotechnol 129-132:586-598.

What is claimed is:
1. A method of preparing lignocellulosic biomass for enzymatic digestion, comprising:
(a) providing lignocellulosic biomass;
(b) mixing said lignocellulosic biomass with a 1 to 4% alkaline peroxide solution at a pH of 10 to 13 to form a slurry;
(c) separating said slurry into a solid precipitate and a supernatant;

(d) washing said solid precipitate to produce a neutralized solid precipitate; and
(e) treating said neutralized solid precipitate with acidic electrolyzed water at a pH of 2 to 4 or alkaline electrolyzed water at a pH from 8 to 13 to prepare the lignocellulosic biomass for enzymatic digestion.

2. The method of claim 1 wherein the lignocellulosic biomass is selected from the group consisting of *Miscanthus* plant material, switchgrass, cord grass, rye grass, reed canary grass, common reed, wheat straw, barley straw, canola straw, oat straw, corn stover, soybean stover, oat hulls, sorghum, rice hulls, sugar cane bagasse, corn fibre, Distiller's Dried Grains with Solubles (DDGS), corn cobs, pine, willow, aspen, poplar wood, and energy cane.

3. The method of claim 2 wherein the lignocellulosic biomass is *Miscanthus* plant material.

4. The method of claim 1 wherein the hydrogen peroxide solution is a 1% solution.

5. The method of claim 4 wherein the pH of the hydrogen peroxide is 11.5.

6. The method of claim 1 wherein the hydrogen peroxide solution is a 2% solution.

7. The method of claim 6 wherein the pH of the hydrogen peroxide is 11.5.

8. The method of claim 1 wherein the hydrogen peroxide solution is a 3% solution.

9. The method of claim 8 wherein the pH of the hydrogen peroxide is 11.5.

10. The method of claim 1 wherein the hydrogen peroxide solution is a 4% solution.

11. The method of claim 10 wherein the pH of the hydrogen peroxide is 11.5.

12. The method of claim 1 wherein said solid precipitate is treated with acidic electrolyzed water at a pH of 2 to 4.

13. The method of claim 12 wherein said solid precipitate is treated with acidic electrolyzed water at a pH of 2.6.

14. The method of claim 1 wherein said solid precipitate is treated with alkaline electrolyzed water at a pH of 8 to 13.

15. The method of claim 14 wherein said solid precipitate is treated with alkaline electrolyzed water at a pH of 11.4.

16. The method of claim 1 wherein step (e) is performed at a temperature of 100 to 140° C.

17. The method of claim 16 wherein step (e) is performed at a temperature of 121° C.

18. A method of hydrolyzing lignocellulosic biomass with an enzyme, comprising:
(a) providing lignocellulosic biomass;
(b) mixing said lignocellulosic biomass with a 1 to 4% alkaline peroxide solution at a pH of 10 to 13 to form a slurry;
(c) separating said slurry into a solid precipitate and a supernatant;
(d) washing said solid precipitate to produce a neutralized solid precipitate;
(e) treating said neutralized solid precipitate with acidic electrolyzed water at a pH of 2 to 4 or alkaline electrolyzed water at a pH of 8 to 13 to form an electrolyzed water-treated precipitate; and
(f) hydrolyzing said electrolyzed water-treated precipitate with an enzyme.

19. The method of claim 18 wherein said enzyme is cellulase.

* * * * *